US011872407B2

United States Patent
Ishikawa et al.

(10) Patent No.: US 11,872,407 B2
(45) Date of Patent: Jan. 16, 2024

(54) APPARATUS FOR GENERATING SIGNAL WAVEFORM FOR BIOLOGICAL STIMULATION

(71) Applicants: NIPRO CORPORATION, Osaka (JP); HARADA ELECTRONICS INDUSTRY CO., LTD., Sapporo (JP)

(72) Inventors: Toshizo Ishikawa, Osaka (JP); Shigenori Tominaga, Osaka (JP); Yoshihiko Sano, Osaka (JP); Masahide Harada, Sapporo (JP)

(73) Assignees: NIPRO CORPORATION, Osaka (JP); HARADA ELECTRONICS INDUSTRY CO., LTD., Sapporo (JP)

( * ) Notice: Subject to any disclaimer, the term of this patent is extended or adjusted under 35 U.S.C. 154(b) by 480 days.

(21) Appl. No.: 16/626,141

(22) PCT Filed: Jun. 8, 2018

(86) PCT No.: PCT/JP2018/021985
§ 371 (c)(1),
(2) Date: Dec. 23, 2019

(87) PCT Pub. No.: WO2018/235629
PCT Pub. Date: Dec. 27, 2018

(65) Prior Publication Data
US 2020/0197717 A1 Jun. 25, 2020

(30) Foreign Application Priority Data
Jun. 23, 2017 (JP) ................................. 2017-123142

(51) Int. Cl.
*A61N 2/02* (2006.01)
*A61N 2/00* (2006.01)

(52) U.S. Cl.
CPC ............... *A61N 2/02* (2013.01); *A61N 2/002* (2013.01); *A61N 2/008* (2013.01)

(58) Field of Classification Search
CPC .......... A61N 2/002; A61N 2/008; A61N 2/02; A61N 2/004; A61N 2/006; A61N 1/36025; A61N 1/36082
See application file for complete search history.

(56) References Cited

U.S. PATENT DOCUMENTS

| 4,875,484 A | 10/1989 | Anzai et al. | |
|---|---|---|---|
| 8,562,506 B2 * | 10/2013 | Nishi | A61N 2/006 600/14 |

(Continued)

FOREIGN PATENT DOCUMENTS

| JP | S63-95073 A | 4/1988 |
|---|---|---|
| JP | H09-047516 A | 2/1997 |

(Continued)

OTHER PUBLICATIONS

Feb. 11, 2021 Search Report issued in European Patent Application No. 18820902.7.

(Continued)

*Primary Examiner* — Christine H Matthews
(74) *Attorney, Agent, or Firm* — Oliff PLC

(57) ABSTRACT

An apparatus for generating signal waveform for biological stimulation capable of generating and outputting a biological stimulation signal wave, from a signal existing in the external environment, reflected from the signal, which includes a signal input unit for inputting an external signal from the external environment and an output waveform generation unit for generating and outputting a first biological stimulation signal wave modulated with at least one of a frequency component, an envelope component and an amplitude component included in the external signal acquired by (Continued)

the signal input unit and/or synchronized with an output timing of the external signal.

9 Claims, 29 Drawing Sheets

(56) References Cited

U.S. PATENT DOCUMENTS

| | | | |
|---|---|---|---|
| 2009/0069626 A1* | 3/2009 | Pilla | A61N 2/004 600/13 |
| 2012/0010559 A1* | 1/2012 | Higgins | A61K 35/16 604/20 |
| 2017/0112408 A1 | 4/2017 | Durand | |

FOREIGN PATENT DOCUMENTS

| | | |
|---|---|---|
| JP | H10-125111 A | 5/1998 |
| JP | H11-249673 A | 9/1999 |
| JP | 2004-229701 A | 8/2004 |
| JP | 2006-304020 A | 11/2006 |
| JP | 2009-266484 A | 11/2009 |
| JP | 2014-113362 A | 6/2014 |
| JP | 2016-144546 A | 8/2016 |
| WO | 2008/109058 A1 | 9/2008 |
| WO | 2017/040741 A1 | 3/2017 |

OTHER PUBLICATIONS

Sep. 11, 2018 International Search Report issued in International Patent Application No. PCT/JP2018/021985.

* cited by examiner

FIG. 4(a) Constant frequency (waveform <1>)
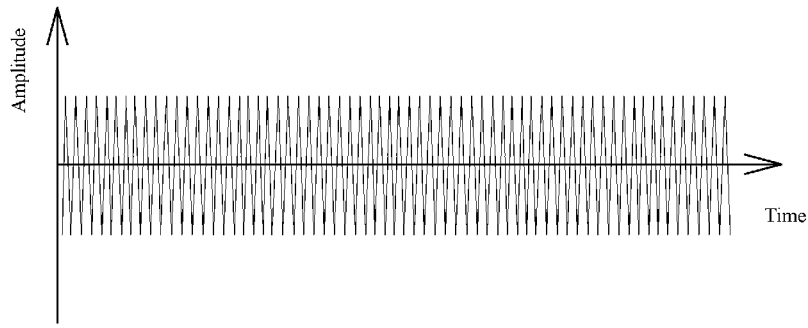
FIG. 4(b) Varied in proportion to external signal frequency (waveform <1>)
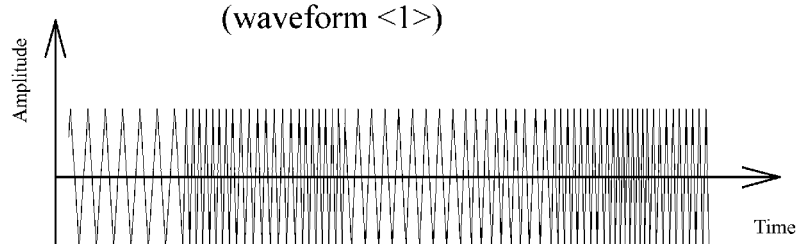
FIG. 4(c) Varied in proportion to external signal envelope (waveform <1>)
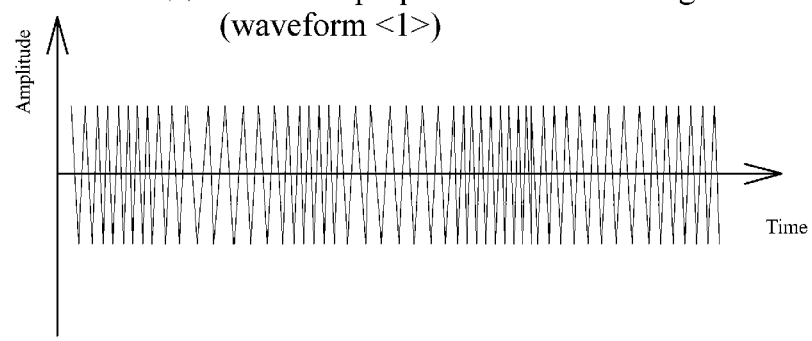
FIG. 4(d) Varied in proportion to external signal amplitude (waveform<1>)
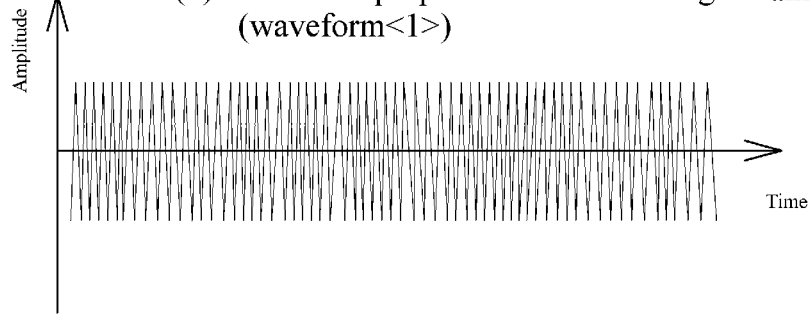

APPARATUS FOR GENERATING SIGNAL WAVEFORM FOR BIOLOGICAL STIMULATION

TECHNICAL FIELD

This invention relates to an apparatus for generating signal waveform for biological stimulation, which generates and outputs biological stimulation signal wave.

BACKGROUND ART

Stimulation applied to a biological body from the external environment includes light, sound, oscillation, temperature and so on. There are various patterns of such stimulation including uncomfortable pattern, comfortable pattern, healing pattern and so on.

There is no disagreement that most people feel comfortable or healed by sound, light or oscillation that they feel from murmuring of a river, sunlight filtered through leaves, Mozart's music and the like. Also, it is well-known that fluctuation of 1/f is detected when signals of these sounds or lights are analyzed.

Considering above, it has been proposed to adopt the 1/f pitch fluctuation in an apparatus for stimulating a biological body such as low-frequency electrotherapy equipment, lighting equipment, electric massager, electric fan or the like (for example, see the following Patent Literatures 1, 2).

It is common to produce signals having the 1/f pitch fluctuation by using computer programs, except ones produced by an electronic circuit.

Focusing only on 1/f fluctuation, pink noise or the like has a complete 1/f fluctuation but is a quite uncomfortable sound when heard as a sound. Thus, it is difficult to generate an effective signal or a signal for comfortability or healing by computer programs. Also, the signal having 1/f fluctuation generated by the computer program is naturally constant as far as the program is not changed.

CITATION LIST

Patent Literature

Patent Literature 1: JP-A-H09-47516
Patent Literature 2: JP-A-2009-266484

SUMMARY OF INVENTION

Technical Problem

It is, therefore, an object of the invention to provide an apparatus for generating signal waveform for biological stimulation, which can generate and output biological stimulation signal wave reflected from signals existing on the external environment such as sunlight filtered through leaves, murmuring of a river, comfortable music or favorite music, mother's heart sound and so on, instead of generating a stimulation signal applied to a biological body artificially by computer programs.

Solution to Problem

The apparatus for generating signal waveform for biological stimulation according to the invention comprises: a signal input unit for inputting an external signal from the external environment, and an output waveform generation unit for generating and outputting the first biological stimulation signal wave modulated with at least one of a frequency component, an envelope component and an amplitude component included in the external signal acquired by the signal input unit and/or synchronized with an output timing of the external signal.

In the apparatus for generating signal waveform for biological stimulation according to the invention, it is preferable that the output waveform generation unit is constructed so as to generate the first biological stimulation signal wave subjected to frequency modulation by at least one of the frequency component, the envelope component and the amplitude component included in the external signal.

In the apparatus for generating signal waveform for biological stimulation according to the invention, it is also preferable that the output waveform generation unit is constructed so as to generate the first biological stimulation signal wave subjected to amplitude modulation by at least one of the envelope component and the amplitude component included in the external signal.

The apparatus for generating signal waveform for biological stimulation according to the invention is preferable to comprise at least one first coil for generating a magnetic field by the feeding of the first biological stimulation signal wave.

In the apparatus for generating signal waveform for biological stimulation according to the invention, it is preferable that the output waveform generation unit is constructed so as to generate the second biological stimulation signal wave based on the external signal and is provided with at least one second coil that generates a magnetic field by the feeding of the second biological stimulation signal wave. In this case, it is preferable that the first coil and the second coil are arranged so as to overlap with each other viewing from an axial direction of the coil. The second coil generates a low-frequency magnetic field that causes the stimulation to transmit sensory nerve through spinal dorsal horn to brain when a low-frequency signal wave is fed as the second biological stimulation signal wave.

The apparatus for generating signal waveform for biological stimulation according to the invention is preferably provided with a haptic output unit for outputting the external signal as sound, image and/or oscillation.

In the apparatus for generating signal waveform for biological stimulation according to the invention, the external signal is preferable to be a sound signal of audible frequency band.

The apparatus for generating signal waveform for biological stimulation according to the invention is preferably provided with a storage unit for storing the external signal acquired in the signal input unit and/or the frequency component, envelope component and amplitude component included in the external signal acquired in the signal input unit. Thus, the biological stimulation signal wave can be generated by taking out the external signal from the storage unit of the apparatus without inputting the external signal from the external environment into the signal input unit each time.

Advantageous Effects of Invention

In the apparatus for generating signal waveform for biological stimulation according to the invention, the output waveform generation unit generates the biological stimulation signal wave modulated with at least one of the frequency component, envelope component and amplitude component in the external signal and/or synchronized with the output timing of the external signal, so that the biological stimulation signal wave reflected with signals existing in the external environment can be generated easily.

BRIEF DESCRIPTION OF DRAWINGS

FIG. 4 is a view showing a basic signal or the first biological stimulation signal wave (waveform <1>) generated by a signal wave generation unit in the apparatus for generating signal waveform for biological stimulation of FIG. 1.

FIG. 7O is a view illustrating an example of generating the first biological stimulation signal wave with a frequency proportional to an envelope of the external signal synchronized with an output timing of a half wave of the external signal by using the apparatus for generating signal waveform for biological stimulation of FIG. 1.

DESCRIPTION OF EMBODIMENTS

Figure 1:
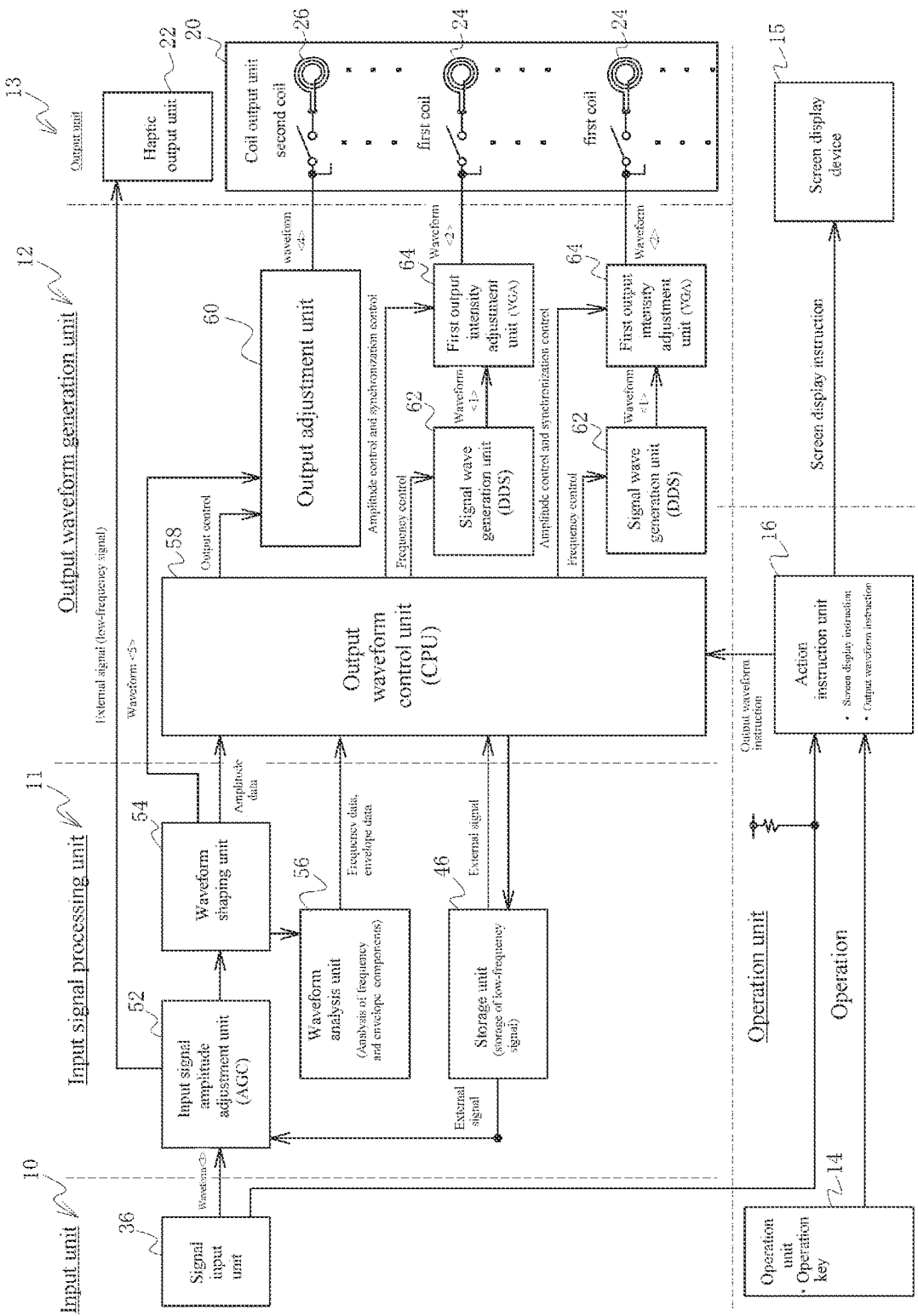
FIG. 1 is a block diagram constituting an apparatus for generating signal waveform for biological stimulation according to an embodiment of the invention.

An embodiment of the invention will be described below in detail with reference to the drawings. FIG. 1 is a block diagram constituting the apparatus for generating signal waveform for biological stimulation according to an embodiment of the invention. The biological body includes a human body. The biological body further includes animals other than the human body.

As shown in FIG. 1, the apparatus for generating signal waveform for biological stimulation according to the embodiment of the invention is mainly constructed with an input unit 10, an input signal processing unit 11, an output waveform generation unit 12, an output unit 13, an operation unit 14 and a screen display device 15. The apparatus for generating signal waveform for biological stimulation is driven by an external power not shown or a battery arrangeable at an inside thereof. The screen display device 15 displays an operation state and an output state in the apparatus for generating signal waveform for biological stimulation under instructions of an action instruction unit 16. The operation unit 14 has various operation keys such as power-supply key, starting key, stopping key, input signal exchange key, output waveform selection key, output coil selection key, output adjustment key and so on.

The output unit 13 has a coil output unit 20 and a haptic output unit 22. The coil output unit 20 has at least one first coil 24 (preferably plural number, e.g. five) for generating a magnetic field by feeding the first biological stimulation signal wave generated by the output waveform generation unit 12, and at least one second coil 26 (preferably plural number, e.g. five) for generating a magnetic field by feeding the second biological stimulation signal wave generated by subjecting an external signal input to the input unit 10 to output adjustment with the output waveform generation unit 12. The first coil 24 and the second coil 26 are preferably arranged so as to overlap with each other viewing from an axial line of the coil, and more preferably, arranged concentrically.

Figure 2:
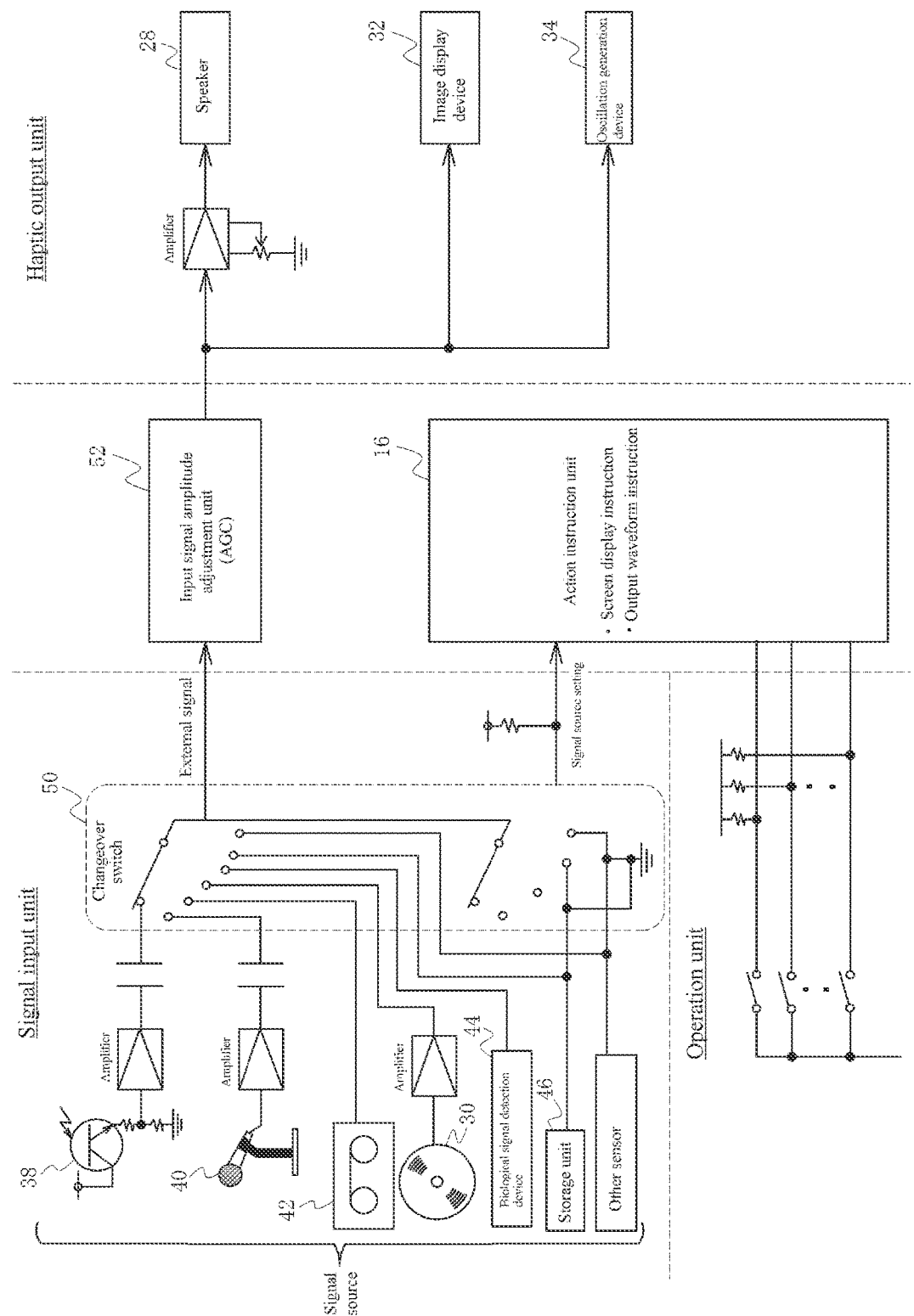
FIG. 2 is a block diagram illustrating a signal input unit and a haptic output unit in the apparatus for generating signal waveform for biological stimulation of FIG. 1.

The haptic output unit 22 may include at least one of a speaker 28 such as a headphone or the like emitting a sound synchronized with an alternating magnetic field generated in the second coil 26 by feeding the external signal amplified with an amplifier; an image display device 32 for projecting an image reproduced in an image reproduction device 30 mentioned later; and an oscillation generation device 34 generating oscillation synchronized with the alternating magnetic field generated by the second coil 26 by inputting the external signal as shown in FIG. 2.

The input unit 10 has a signal input unit 36 as shown in FIG. 1. Into the signal input unit 36 is fed and input an external signal from an inside of the apparatus or various external signal sources. The external signal means an electric signal acquired when a light, a sound (inclusive of music), an oscillation, a temperature or the like present in the external environment or derived from the external environment is detected by various well-known sensors, or an electric signal acquired when a music or the like is reproduced by a well-known reproduction device such as CD player or the like. As an example of the light, sound, oscillation and the like present in the external environment or derived from the external environment may be mentioned sunlight filtered through leaves, murmuring of a river, wind, music, mother's heart sound and so on. The external signal may be a signal stored in the after-mentioned memory unit 46 inside the apparatus. Also, the external signal may be an electric signal acquired from sounds of audible frequency band (10 Hz to several tens of thousands of Hz), preferably kHz band, more preferably 1 kHz to 3 kHz. As shown in FIG. 2, a signal source may include at least one of a light sensor 38, an acoustic sensor 40, an acoustic reproduction device 42, an image reproduction device 30 for reproducing an image inclusive of sound, a biological signal detection device 44 for measuring a biological signal such as brain wave, electrocardiogram, pulse or the like, an oscillation sensor (not shown), a temperature sensor (not shown) and a storage unit 46 inside the apparatus. The storage unit 46 stores the external signal acquired by the signal input unit 36 and/or the frequency component, envelope component and amplitude component included in the external signal acquired by the signal input unit 36. Thus, the first and second signal waves for biological stimulation can be generated by taking out the external signal from the storage unit 46 inside the apparatus without inputting the external signal from the external environment to the signal input unit 36 each time. Each signal source is connected to an input signal amplitude adjustment unit 52 mentioned later through a changeover switch 50. The signal sources can be changed over by operating input signal changeover keys in the operation unit 14, and setting of the signal source is output from the changeover switch 50 to the action instruction unit 16.

Figure 3:
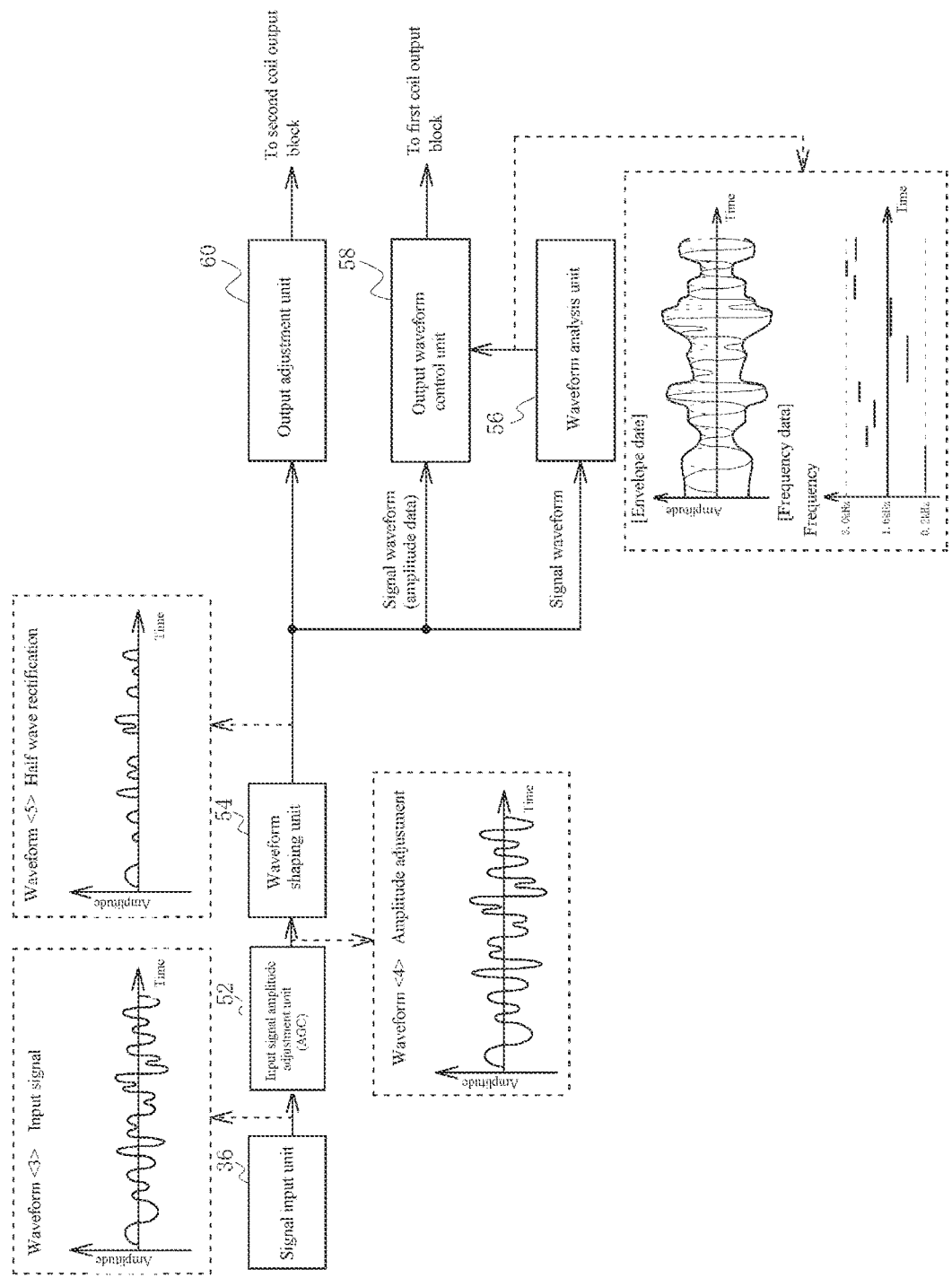
FIG. 3 is a block diagram illustrating an input signal processing unit in the apparatus for generating signal waveform for biological stimulation of FIG. 1, together with waveforms.

As shown in FIGS. 1 and 3, the input signal processing unit 11 is a unit of processing and analyzing the external signal input from any one of the aforementioned signal sources to extract the frequency component, envelope component and amplitude component included in the external signal, and is provided with an input signal amplitude adjustment unit 52, a waveform shaping unit 54 and a waveform analysis unit 56.

The input signal amplitude adjustment unit 52 is, for example, constructed with an automatic gain controller (AGC) and conducts an amplitude adjustment for the external signal (waveform <3>) input to the signal input unit 36 to form a waveform <4>.

The waveform shaping unit 54 forms a waveform <5> by half-wave rectification of the external signal subjected to amplitude adjustment through the input signal amplitude adjustment unit 52.

The waveform analysis unit 56 analyzes frequency and envelops of the external signal and outputs the resulting frequency data and envelope data to the after-mentioned output waveform control unit 58 in the output waveform generation unit 12. The amplitude data of the external signal are output from the waveform shaping unit 54 to an output waveform control unit 58 in the output waveform generation unit 12. The external signal rectified to half wave by the waveform shaping unit 54 is output to the after-mentioned output adjustment unit 60 in the output waveform generation unit 12 and fed to the second coil 26 as a second biological stimulation signal wave after the amplitude adjustment.

As shown in FIG. 1, the output waveform generation unit 12 comprises the output waveform control unit 58, at least one signal wave generation unit 62 (two in the illustrated example), at least one first output intensity adjustment unit 64 (two in the illustrated example) and the output adjustment unit 60. The signal wave generation unit 62 is, for example, constructed with a direct digital synthesizer (DDS), which oscillates a basic signal of an arbitrary frequency from, for example, a band of 30 MHz to 300 MHz and generates the first biological stimulation signal wave by modulation of the basic signal or the like as mentioned later. Also, the first output intensity adjustment unit 64 is, for example, constructed with a variable gain amplifier (VGA).

The output waveform control unit 58 is, for example, constructed with a CPU (central processing unit) and outputs a control signal for conducting the output adjustment of the output adjustment unit 60. Also, the output waveform control unit 58 outputs a control signal for outputting a basic signal of a certain frequency or the first biological stimulation signal wave formed by subjecting the basic signal to frequency modulation with at least one of the frequency component, envelop component and amplitude component of the external signal, to the signal wave generation unit 62. FIG. 4 exemplifies the basic signal oscillated in the signal wave generation unit 62 or the first biological stimulation signal wave (waveform <1>). FIG. 4 (*a*) is a basic signal oscillated at a certain frequency, and FIG. 4(*b*) is the first biological stimulation signal wave generated by varying the basic signal so as to be proportional to the frequency component of the external signal, and FIG. 4(*c*) is the first biological stimulation signal wave generated by varying the basic signal so as to be proportional to the envelope component of the external signal, and FIG. 4(*d*) is the first biological stimulation signal wave generated by varying the basic signal so as to be proportional to the amplitude component of the external signal.

Further, the output waveform control unit 58 outputs a control signal for amplitude control and synchronous control in the first output intensity adjustment unit 64. The first output intensity adjustment unit 64 outputs the first biological stimulation signal wave generated in the signal wave generation unit 62 at a constant amplitude or at a state of modulated with the envelope component or amplitude component of the external signal under the control of the output waveform control unit 58. Further, the first output intensity adjustment unit 64 outputs the first biological stimulation signal wave, instead of the amplitude modulation or in addition thereto, in synchronization with the output timing of the external signal to the first coil 24.

Figure 5:
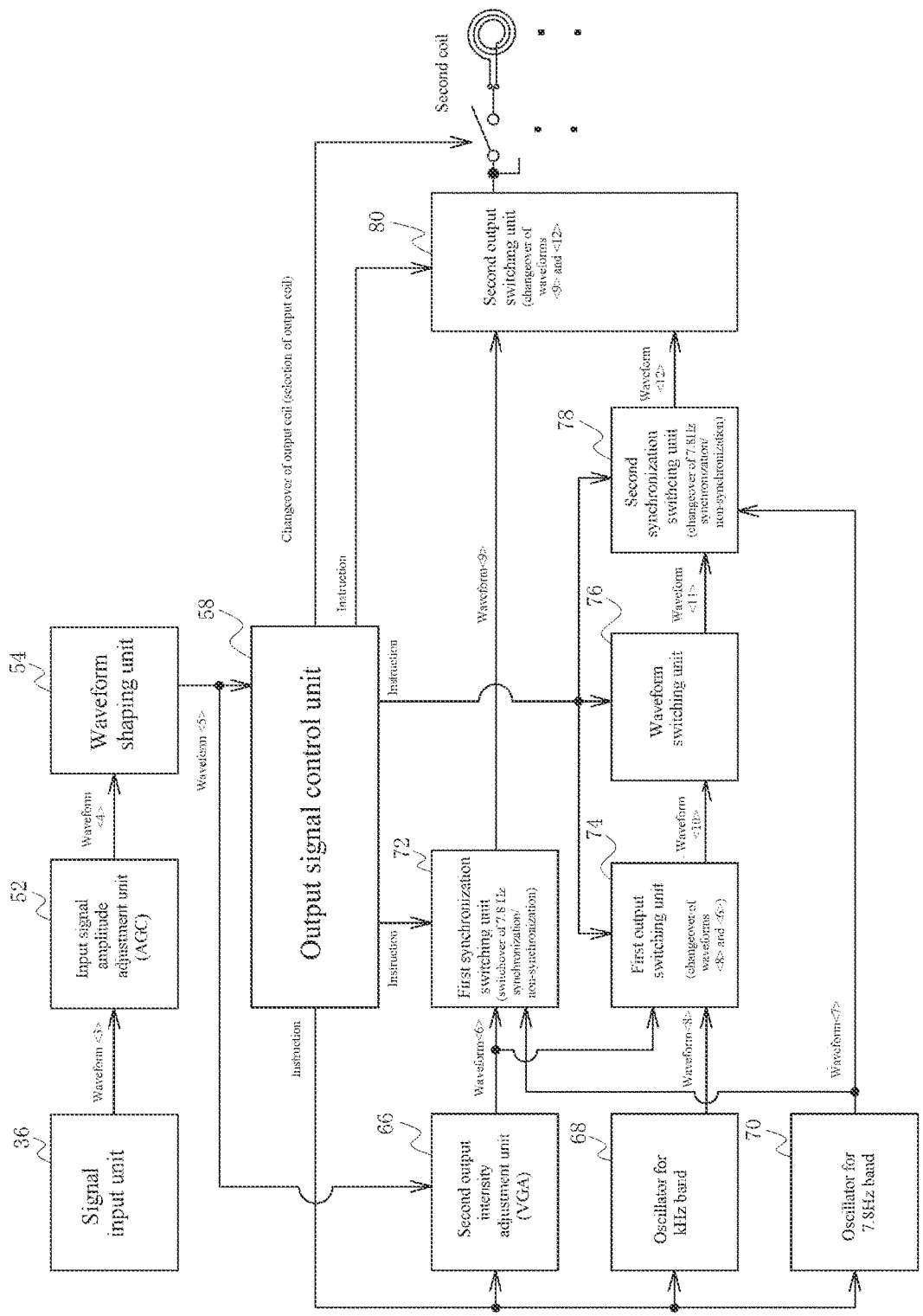
FIG. 5 is a block diagram illustrating an output adjustment unit of the second biological stimulation signal wave in the apparatus for generating signal waveform for biological stimulation of FIG. 1.
Figure 6:
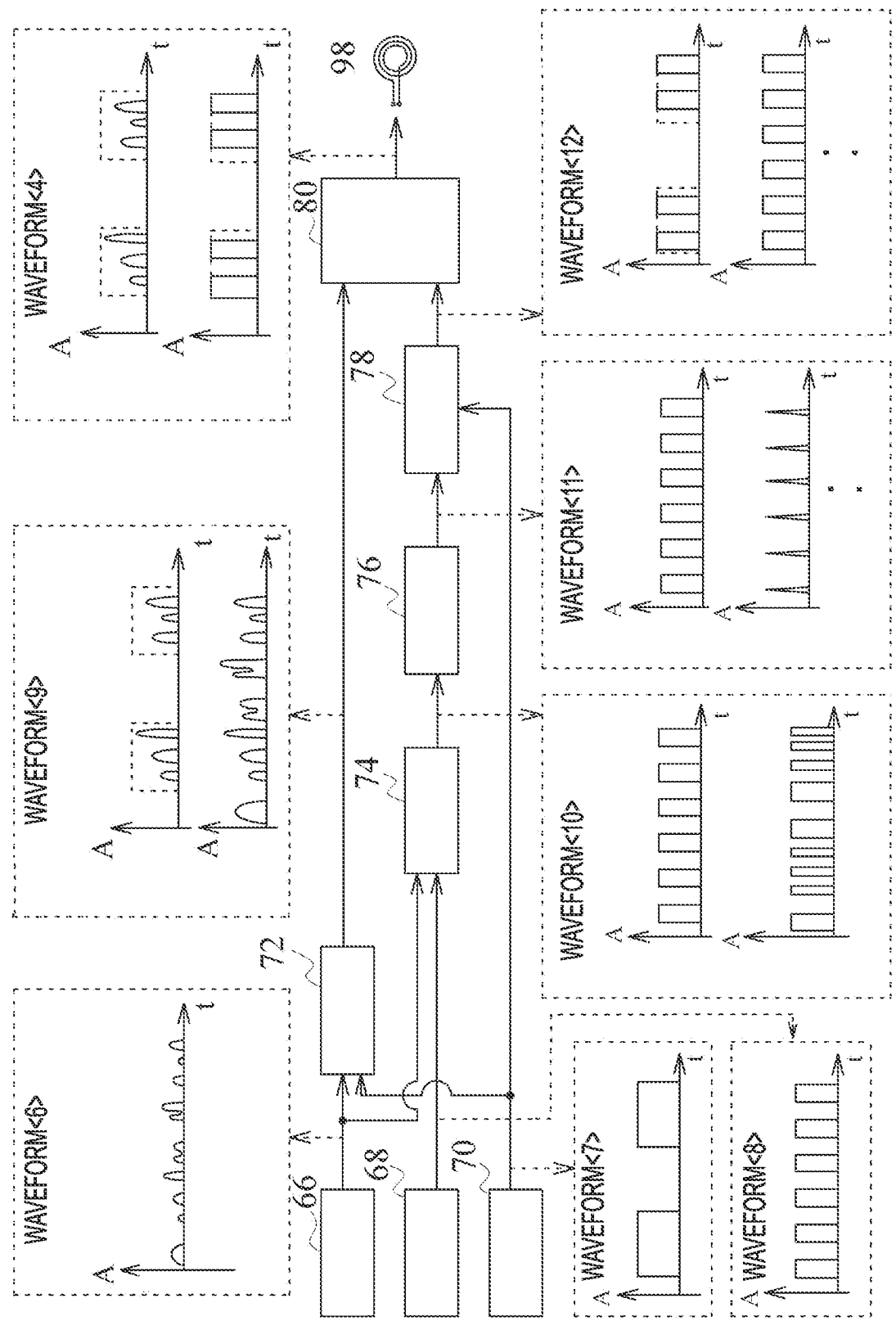
FIG. 6 is a block diagram illustrating the output adjustment unit of the second biological stimulation signal wave in the apparatus for generating signal waveform for biological stimulation of FIG. 1, together with waveforms.

FIG. 5 is a block diagram illustrating the output adjustment unit 60 in the apparatus for generating signal waveform for biological stimulation of FIG. 1, and FIG. 6 is a view illustrating a block configuration of the output adjustment unit 60 together with waveforms. The output adjustment unit 60 comprises the second output intensity adjustment unit 66, an oscillator 68 for kHz band, an oscillator 70 for 7.8 Hz band, the first synchronization switching unit 72, a first output switching unit 74, a waveform switching unit 76, a second synchronization switching unit 78, and a second output switching unit 80.

The second output intensity adjustment unit 66 is, for example, constructed with a variable gain amplifier (VGA) and amplifies the amplitude of the external signal (waveform <5>) rectified to half wave by the waveform shaping unit 54 based on an instruction from the output waveform control unit 58 (waveform <6>).

The oscillator 68 for kHz band generates a signal for kHz band based on an instruction from the output waveform control unit 58 (waveform <8>). The oscillator 70 for 7.8 Hz band generates a signal for 7.8 Hz band based on an instruction from the output waveform control unit 58 (waveform <7>).

The first synchronization switching unit 72 switches over synchronization/non-synchronization of the second biological stimulation signal wave subjected to amplitude adjustment by the second output intensity adjustment unit 66 with the signal generated in the oscillator 70 for 7.8 Hz band based on an instruction form the output waveform control unit 58 (waveform <9>).

The first output switching unit 74 conducts switching between a signal for kHz band generated in the oscillator 68 for kHz band (waveform <8>) and a rectangular digital waveform signal synchronized with the second biological stimulation signal wave (waveform <6>) based on an instruction from the output waveform control unit 58, and outputs to the waveform switching unit 76 (waveform <10>).

The waveform switching unit 76 switches over a waveform of a signal sent from the first output switching unit 74 (waveform <10>) to a rectangular waveform, a waveform of impulse or the like based on an instruction from the output waveform control unit 58, and outputs to the second synchronization switching unit 78 (waveform <11>).

The second synchronization switching unit 78 switches over synchronization/non-synchronization of the waveform of signal sent from the waveform switching unit 76 (waveform <11>) with signal generated in the oscillator 70 for 7.8 Hz band, based on an instruction from the output waveform control unit 58 (waveform <12>).

The second output switching unit 80 conducts switching between the analog waveform signal from the first synchronization switching unit 72 (waveform <9>) and the digital waveform signal from the second synchronization switching unit 78 (waveform <12>), and outputs to the second coil 26.

The output waveform control unit 58 outputs the second biological stimulation signal wave to the second coil 26 selected through the operation of coil selection key by a user. The second biological stimulation signal wave can be fed to all of second coils 26 but can be fed to only a part of the second coils 26.

In order to directly apply magnetic stimulation to nerve by irradiating a magnetic field to a biological body with the thus constructed apparatus for generating signal waveform for biological stimulation, the first coil 24 and the second coil 26 are set and fixed to the skin of a human body or an animal, or the periphery thereof with an adhesive pad, a magic belt or tape, a seal, a gel or the like. The first coil 24 and the second coil 26 may be housed in the same probe. The first coil 24 and the second coil 26 may be used in plural sets in accordance with a stimulation applying range or the like. The method of fixing the first coil 24 and the second coil 26 to the biological body is not limited to the above and may be performed by housing into a pocket or the like of a clothing.

Various operation keys in the operation unit 14 are operated to perform adjustment of signal source, output waveform, output coil and output. When the start key is operated, an external signal fed from the selected signal source, which may be a low frequency signal of 1 kHz to 3 kHz band, is first shaped in the input signal processing unit 11, then subjected to output adjustment in the output adjustment unit 60, and thereafter fed to the second coil 26 as a second biological stimulation signal wave to generate an alternating magnetic field based on the second biological stimulation signal wave.

On the other hand, a basic signal or the first biological stimulation signal wave, which may be of a high frequency, shown in any one of FIGS. 4(a) to 4(d) is generated in accordance with a selected output waveform in the signal wave generation unit 62. The basic signal or the first biological stimulation signal wave generated in the signal wave generation unit 62 is subjected to amplitude modulation with an envelope or amplitude of the external signal in the first output intensity adjustment unit 64 and/or output to the first coil 24 in synchronization with an output timing of the external signal to generate an alternating magnetic field based on the first biological stimulation signal wave.

Figure 7A:
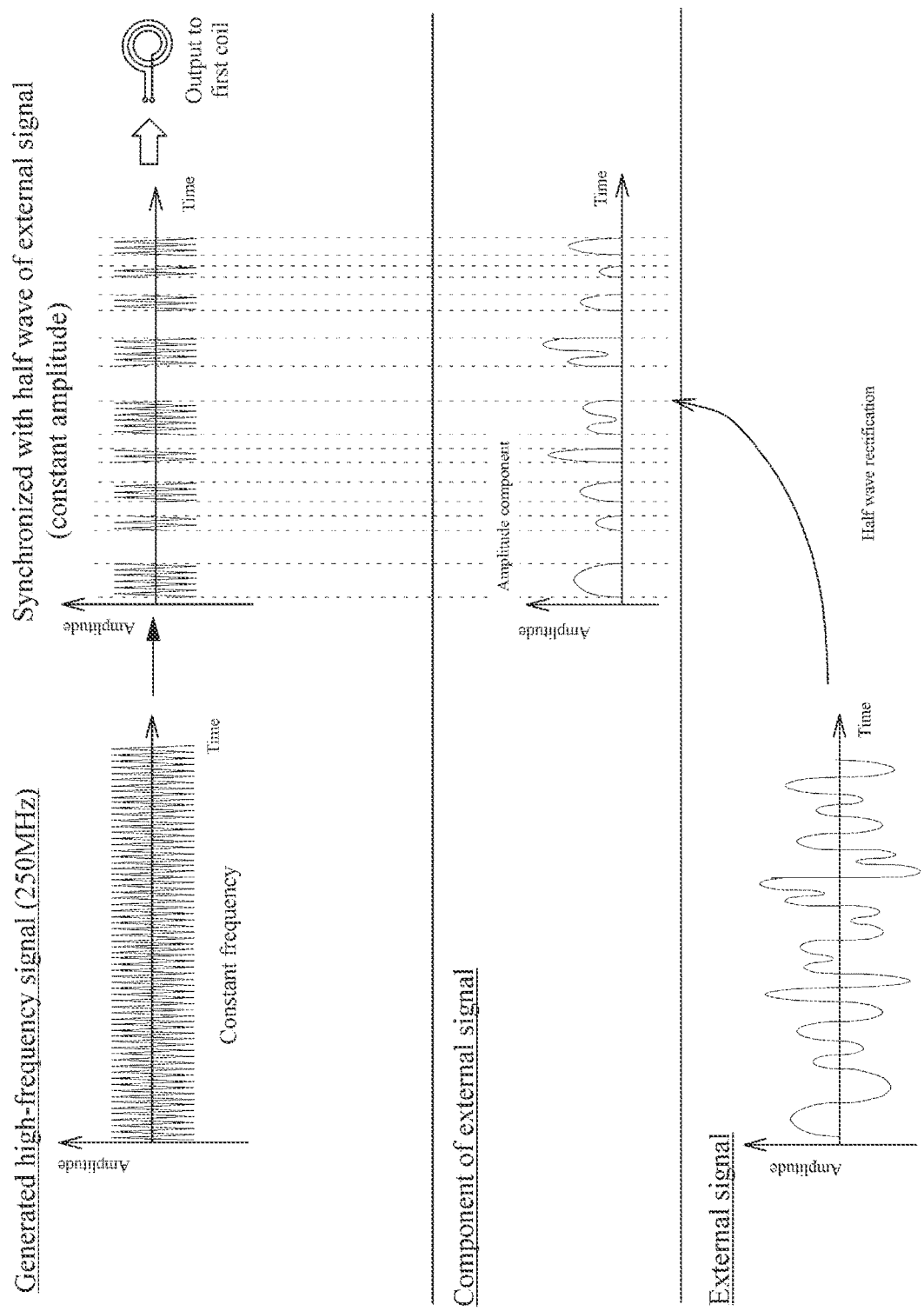
FIG. 7A is a view illustrating an example of generating the first biological stimulation signal wave synchronized with a half wave of an external signal by using the apparatus for generating signal waveform for biological stimulation of FIG. 1.
Figure 7B:
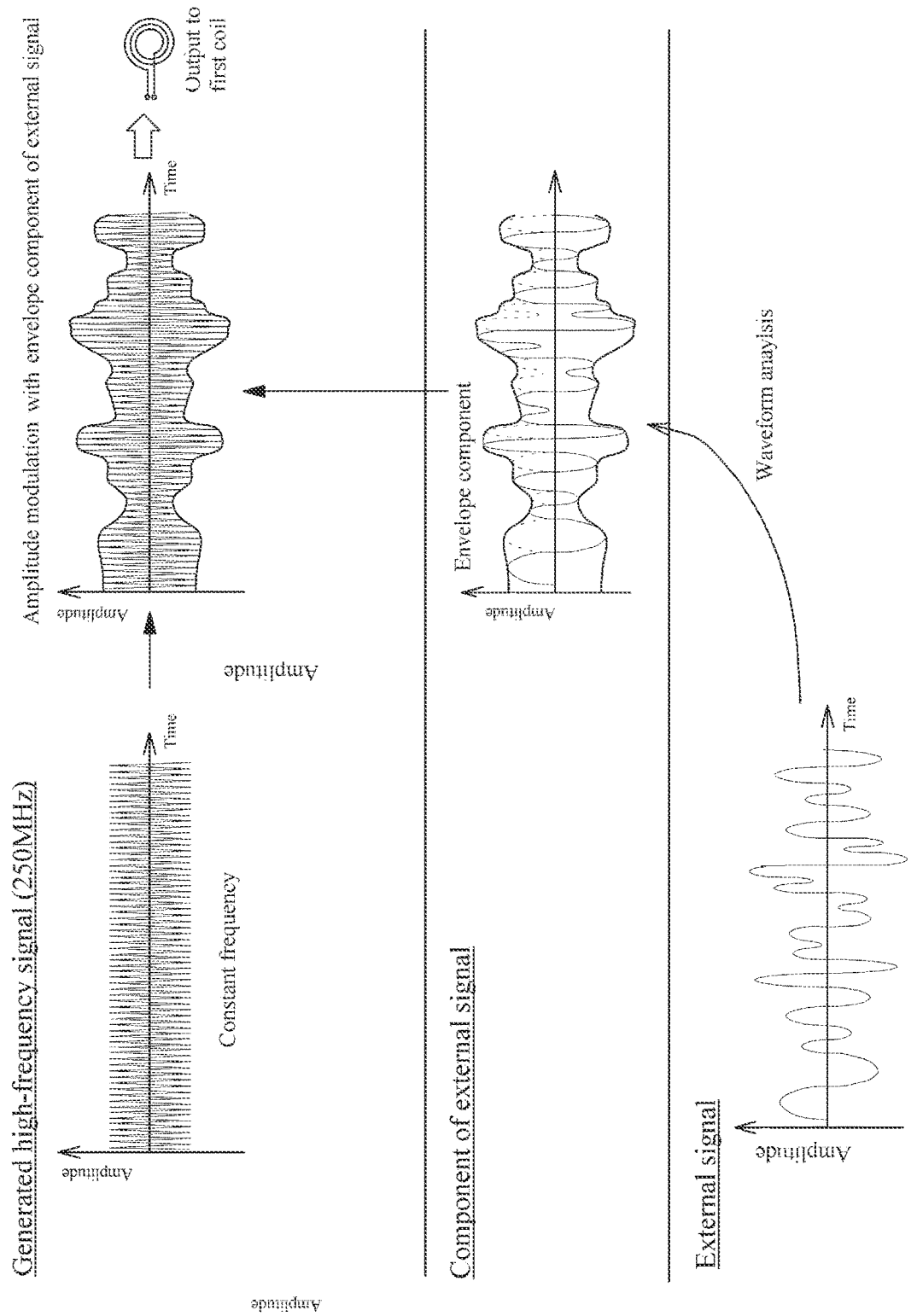
FIG. 7B is a view illustrating an example of generating the first biological stimulation signal wave subjected to amplitude modulation with an envelope of an external signal by using the apparatus for generating signal waveform for biological stimulation of FIG. 1.
Figure 7C:
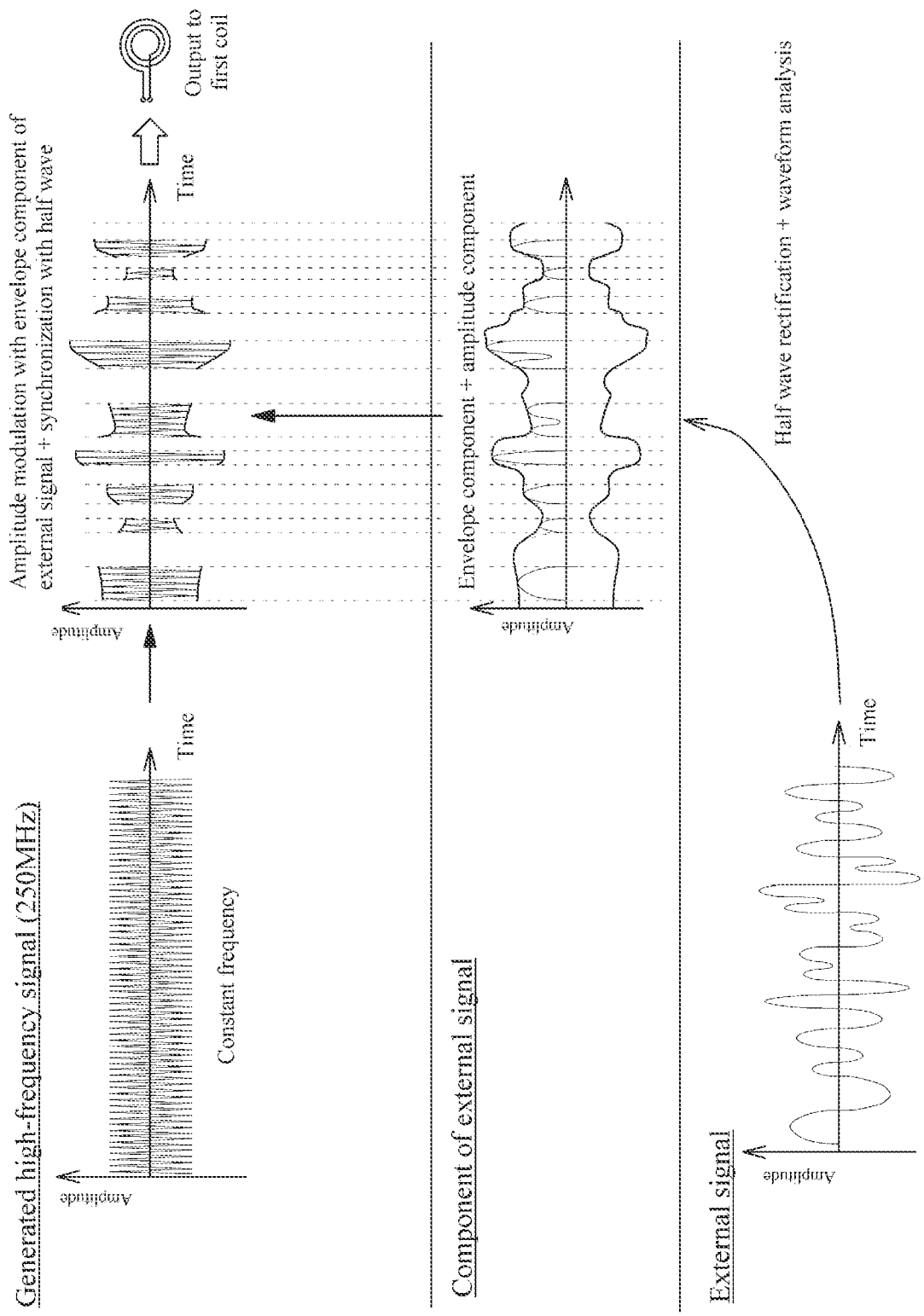
FIG. 7C is a view illustrating an example of generating the first biological stimulation signal wave subjected to amplitude modulation with an envelope of an external signal and also synchronized with an output timing of a half wave of the external signal by using the apparatus for generating signal waveform for biological stimulation of FIG. 1.
Figure 7D:
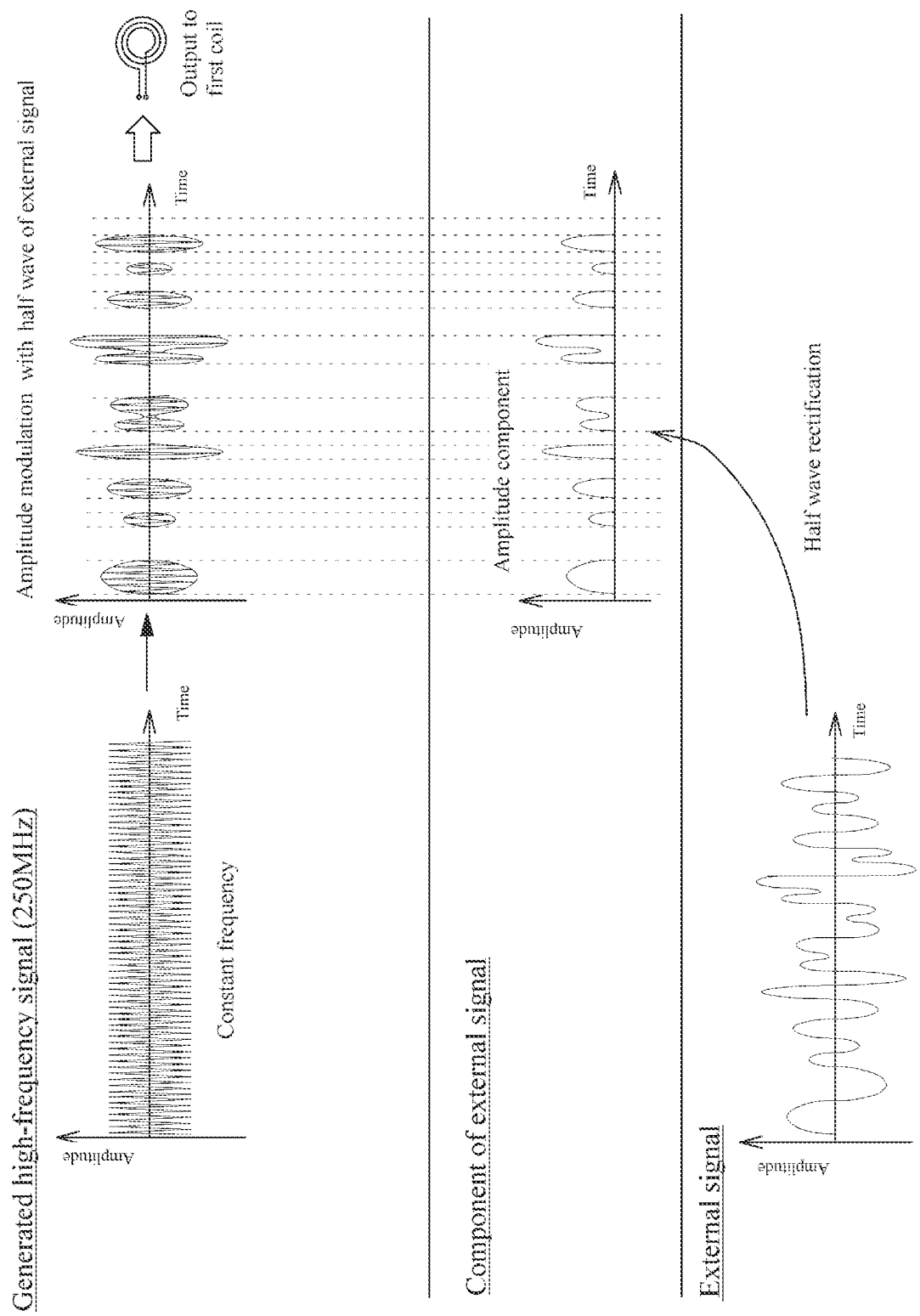
FIG. 7D is a view illustrating an example of generating the first biological stimulation signal wave subjected to amplitude modulation with a half wave of the external signal by using the apparatus for generating signal waveform for biological stimulation of FIG. 1.
Figure 7E:
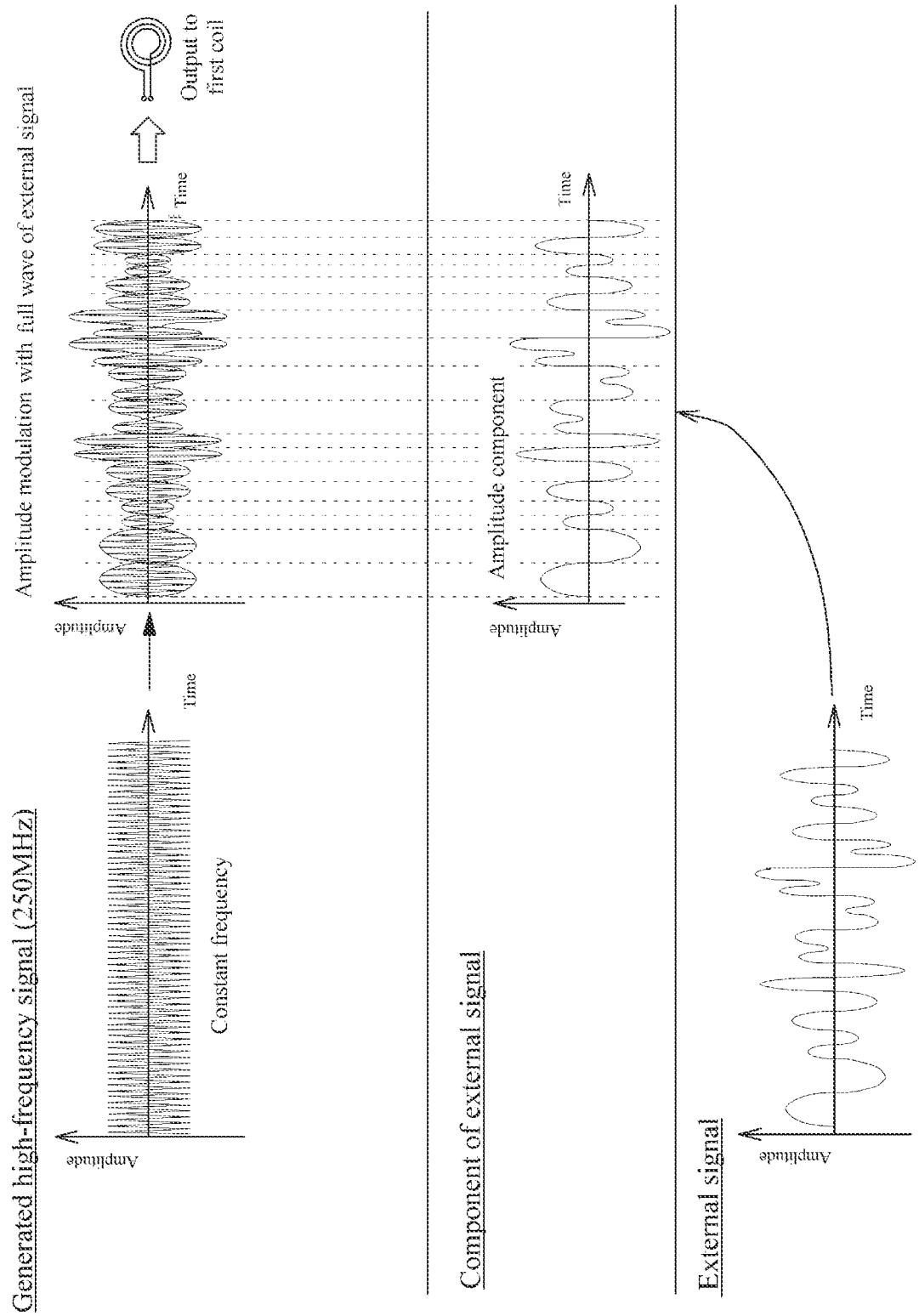
FIG. 7E is a view illustrating an example of generating the first biological stimulation signal wave subjected to amplitude modulation with a full wave of the external signal by using the apparatus for generating signal waveform for biological stimulation of FIG. 1.
Figure 7F:
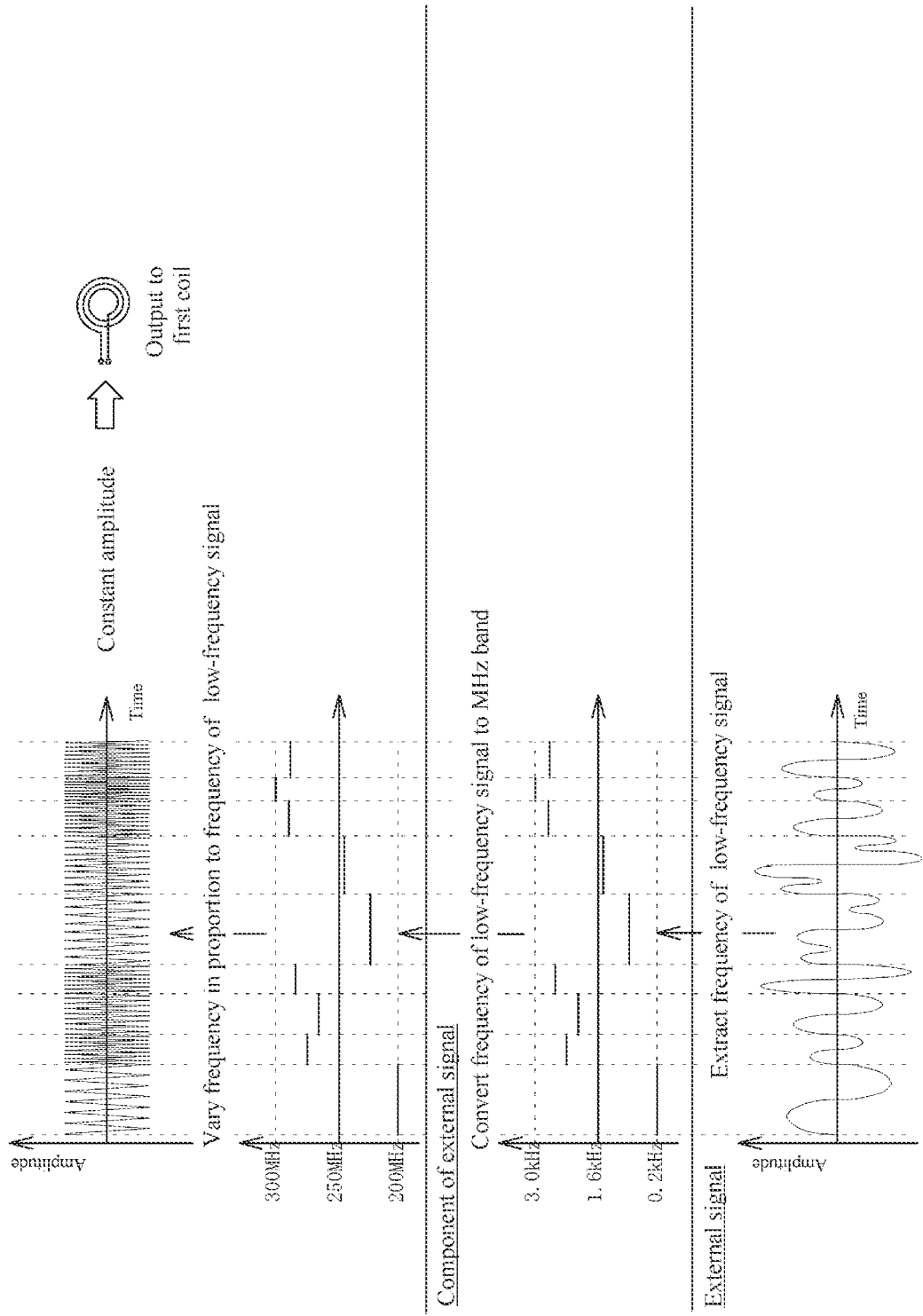
FIG. 7F is a view illustrating an example of generating the first biological stimulation signal wave having a frequency proportional to a frequency of the external signal converted to MHz band by using the apparatus for generating signal waveform for biological stimulation of FIG. 1.
Figure 7G:
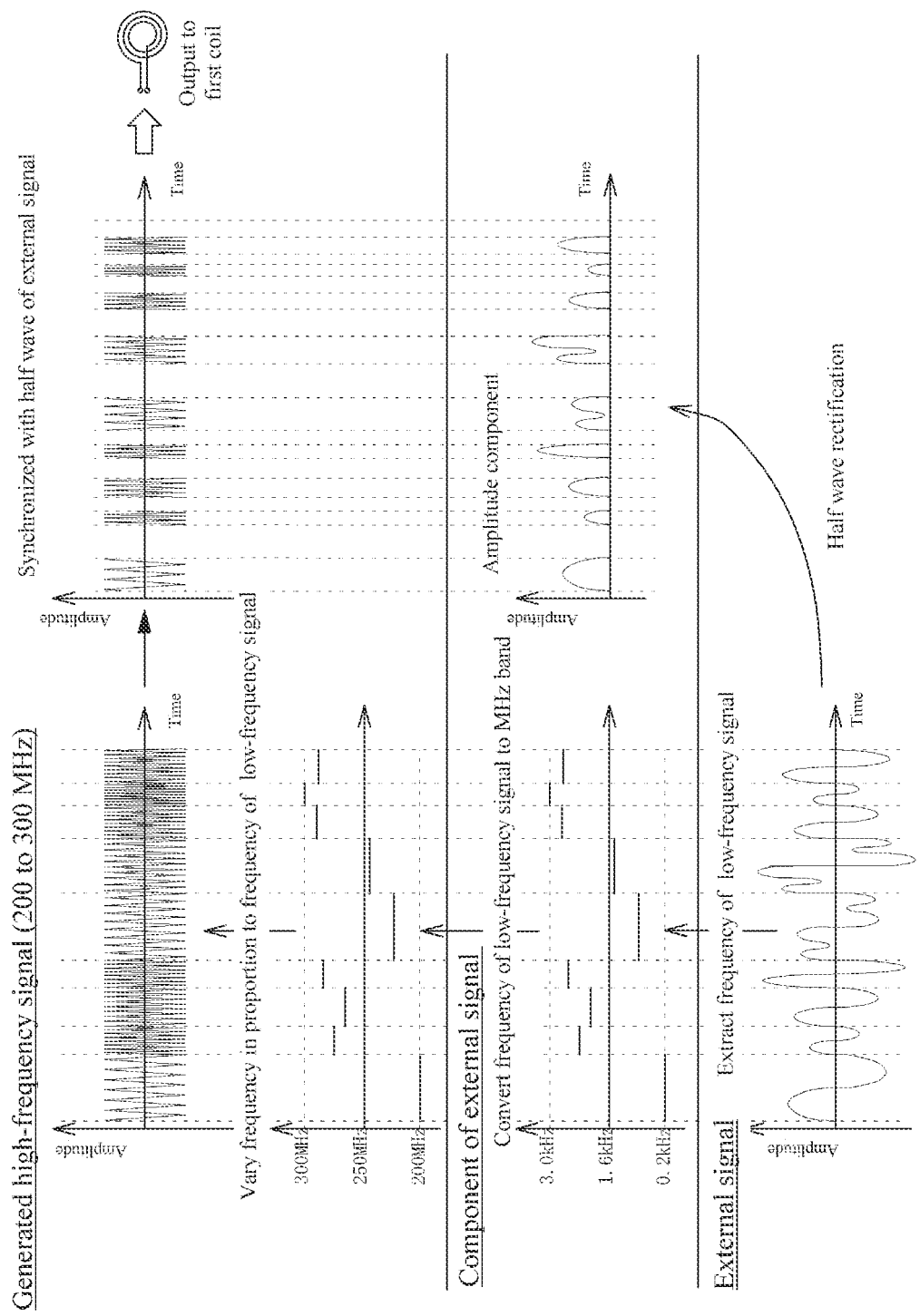
FIG. 7G is a view illustrating an example of generating the first biological stimulation signal wave having a frequency proportional to a frequency of the external signal synchronized with an output timing of a half wave of the external signal by using the apparatus for generating signal waveform for biological stimulation of FIG. 1.
Figure 7H:
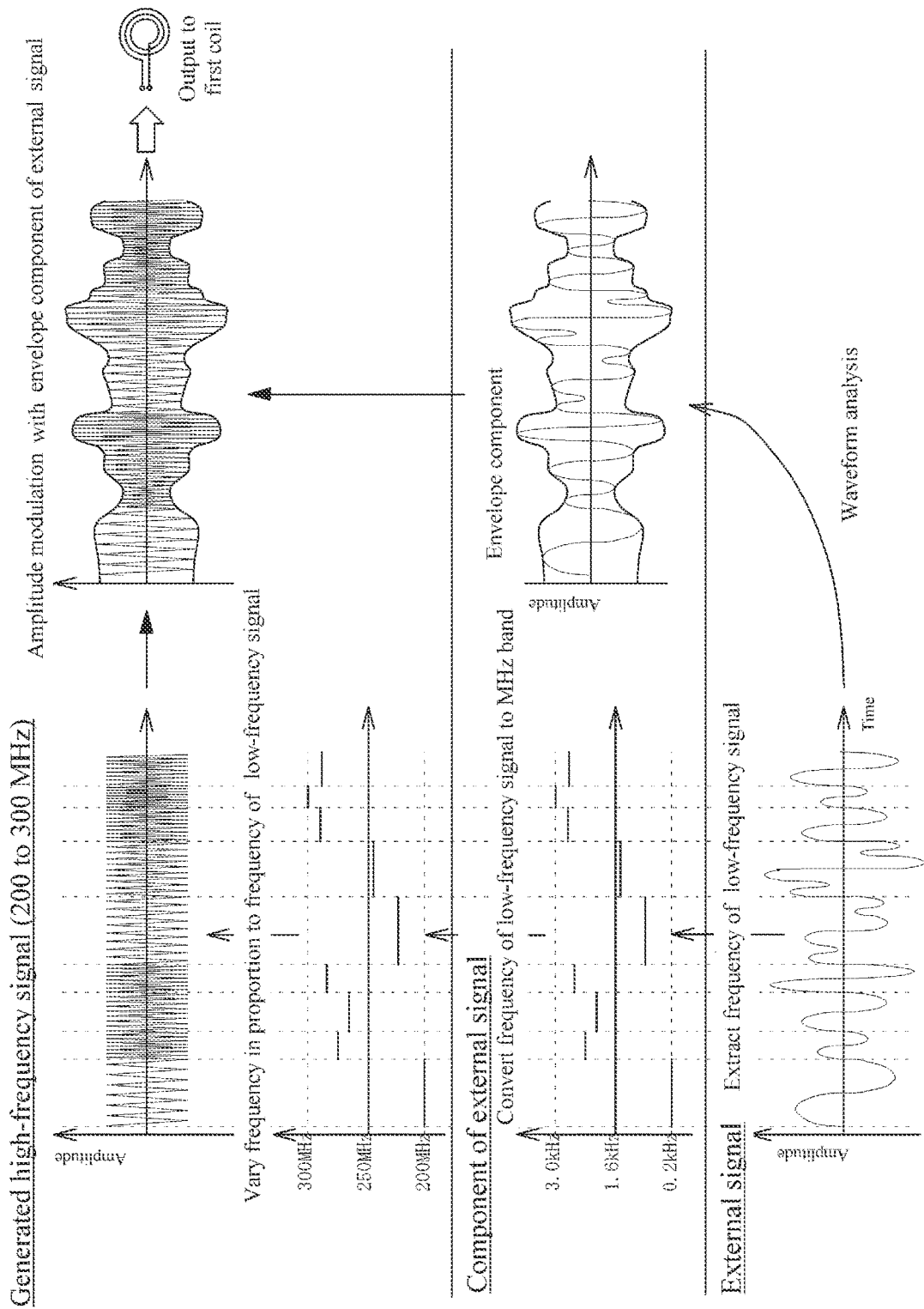
FIG. 7H is a view illustrating an example of generating the first biological stimulation signal wave having a frequency proportional to a frequency of the external signal subjected to amplitude modulation with an envelope of the external signal by using the apparatus for generating signal waveform for biological stimulation of FIG. 1.
Figure 7I:
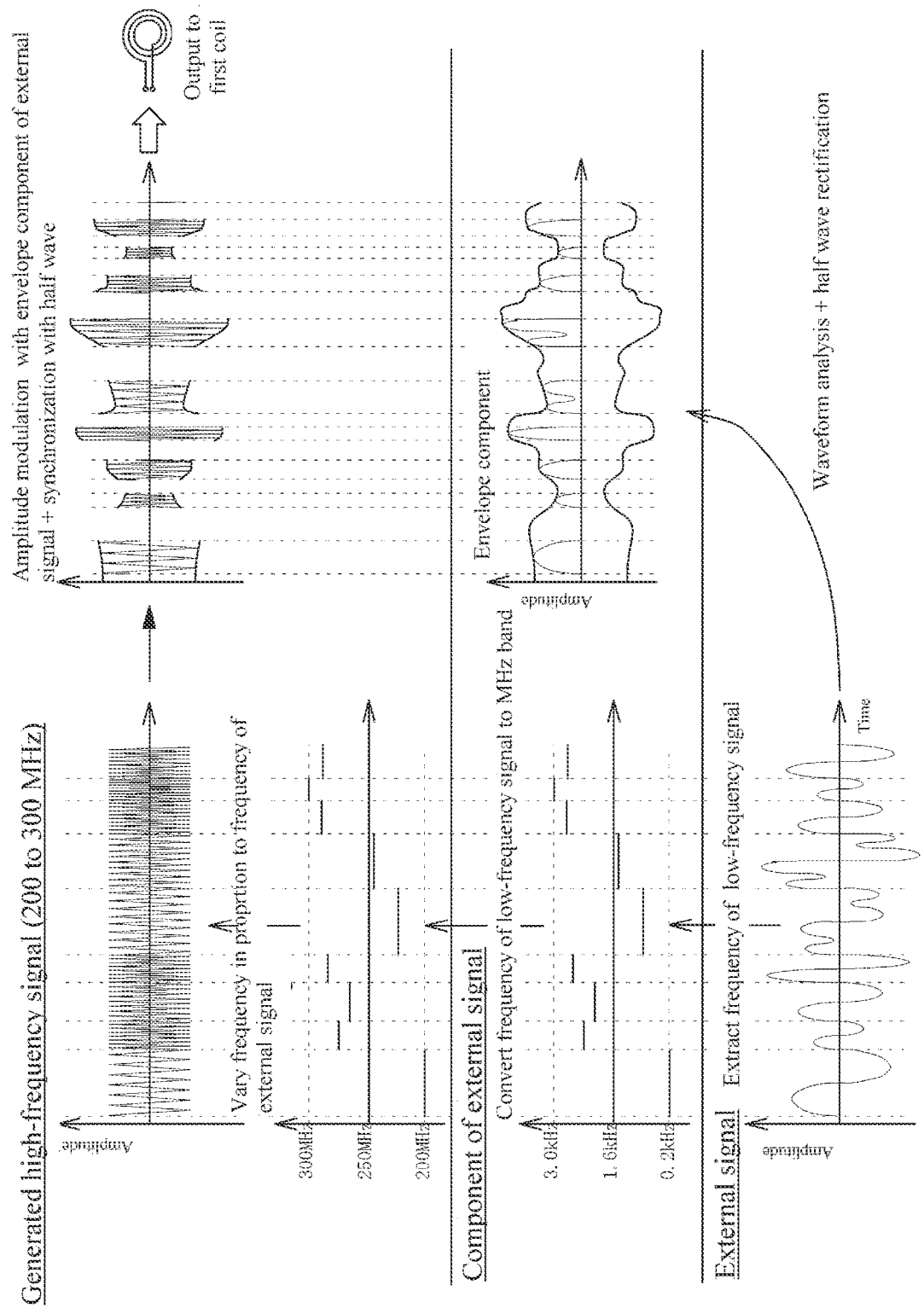
FIG. 7I is a view illustrating an example of generating the first biological stimulation signal wave having a frequency proportional to a frequency of the external signal subjected to amplitude modulation with an envelope of the external signal and synchronized with an output timing of a half wave of the external signal by using the apparatus for generating signal waveform for biological stimulation of FIG. 1.
Figure 7J:
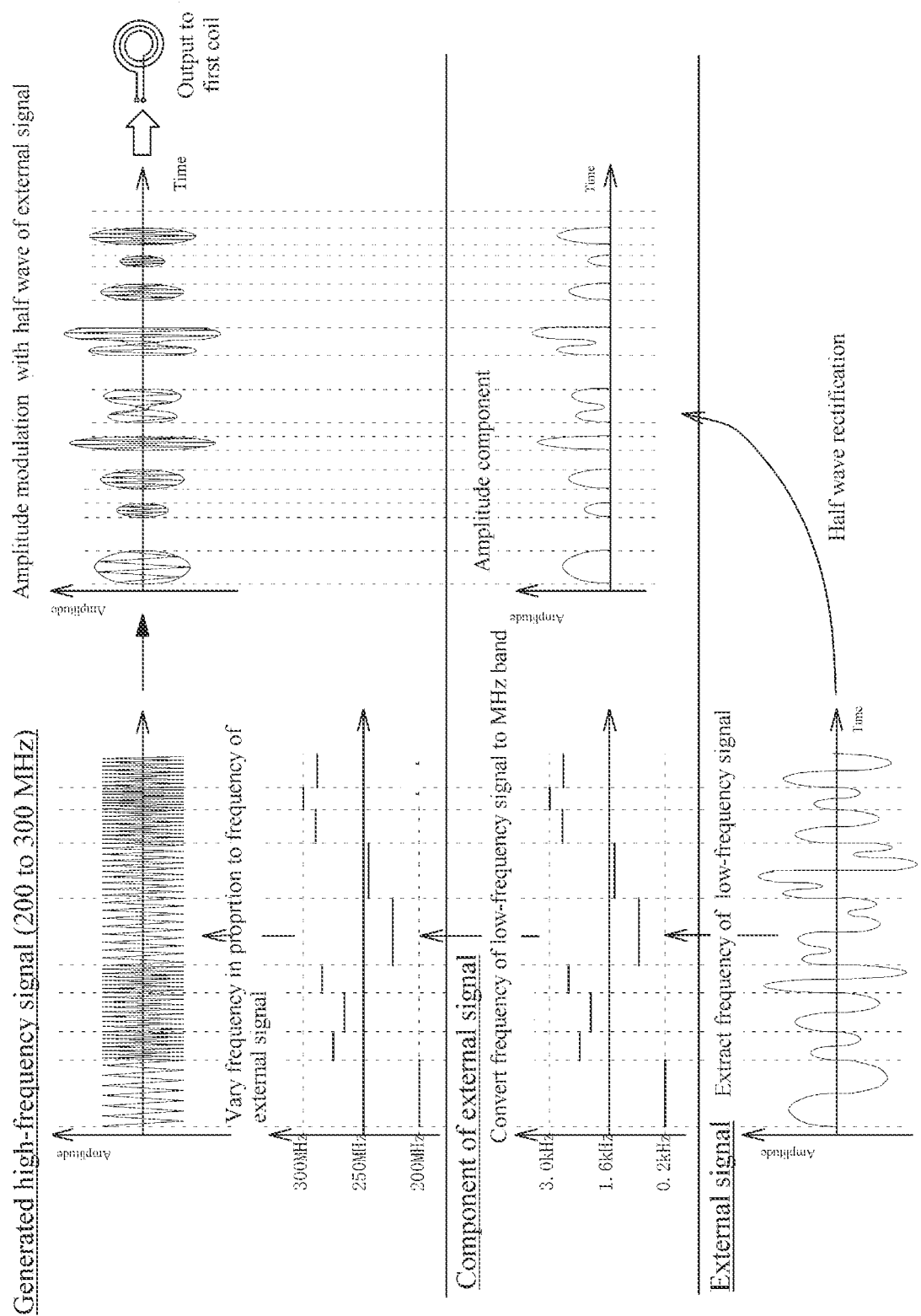
FIG. 7J is a view illustrating an example of generating the first biological stimulation signal wave having a frequency proportional to a frequency of the external signal subjected to amplitude modulation with a half wave of the external signal by using the apparatus for generating signal waveform for biological stimulation of FIG. 1.
Figure 7K:
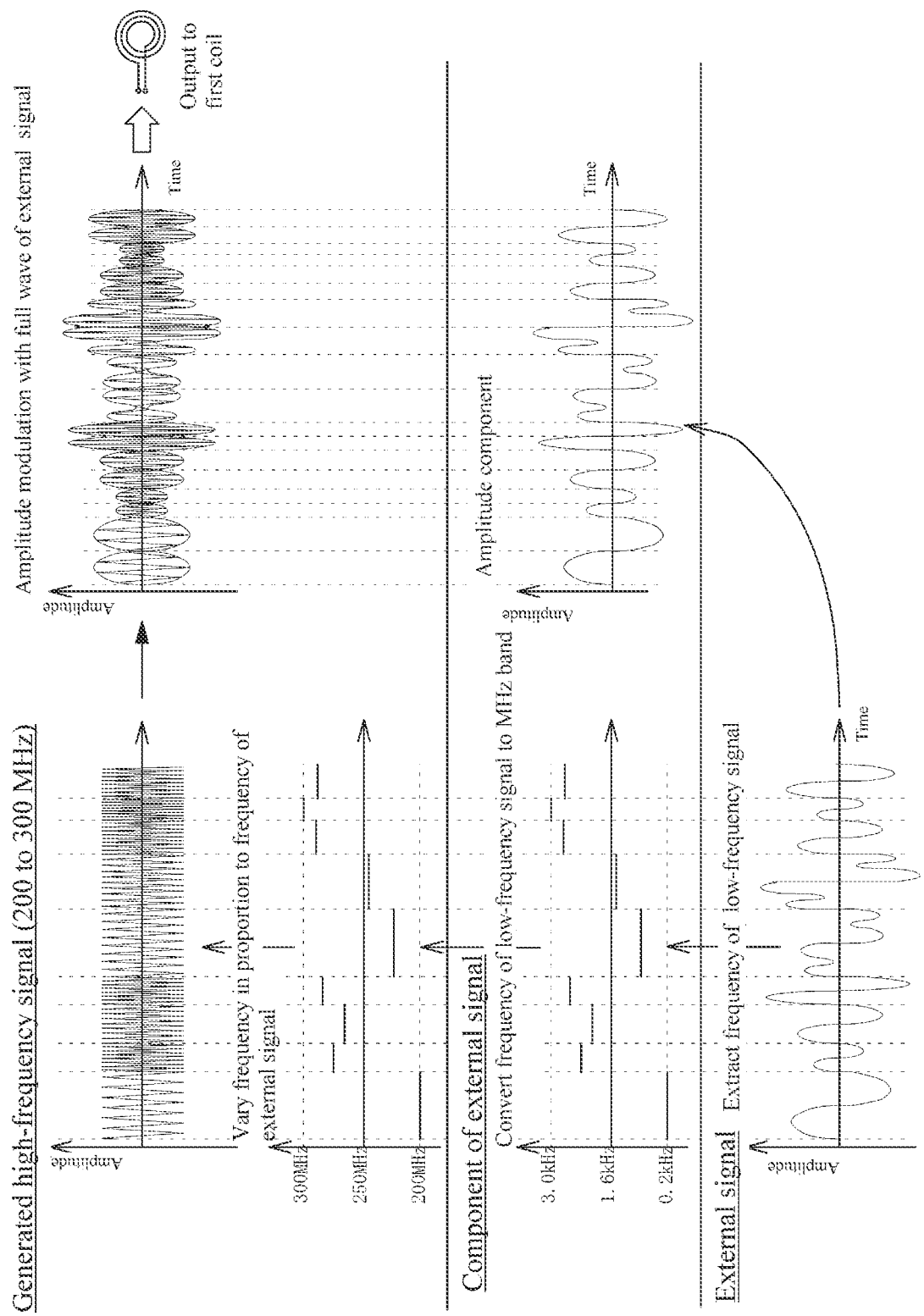
FIG. 7K is a view illustrating an example of generating the first biological stimulation signal wave having a frequency proportional to a frequency of the external signal subjected to amplitude modulation with a full wave of the external signal by using the apparatus for generating signal waveform for biological stimulation of FIG. 1.
Figure 7L:
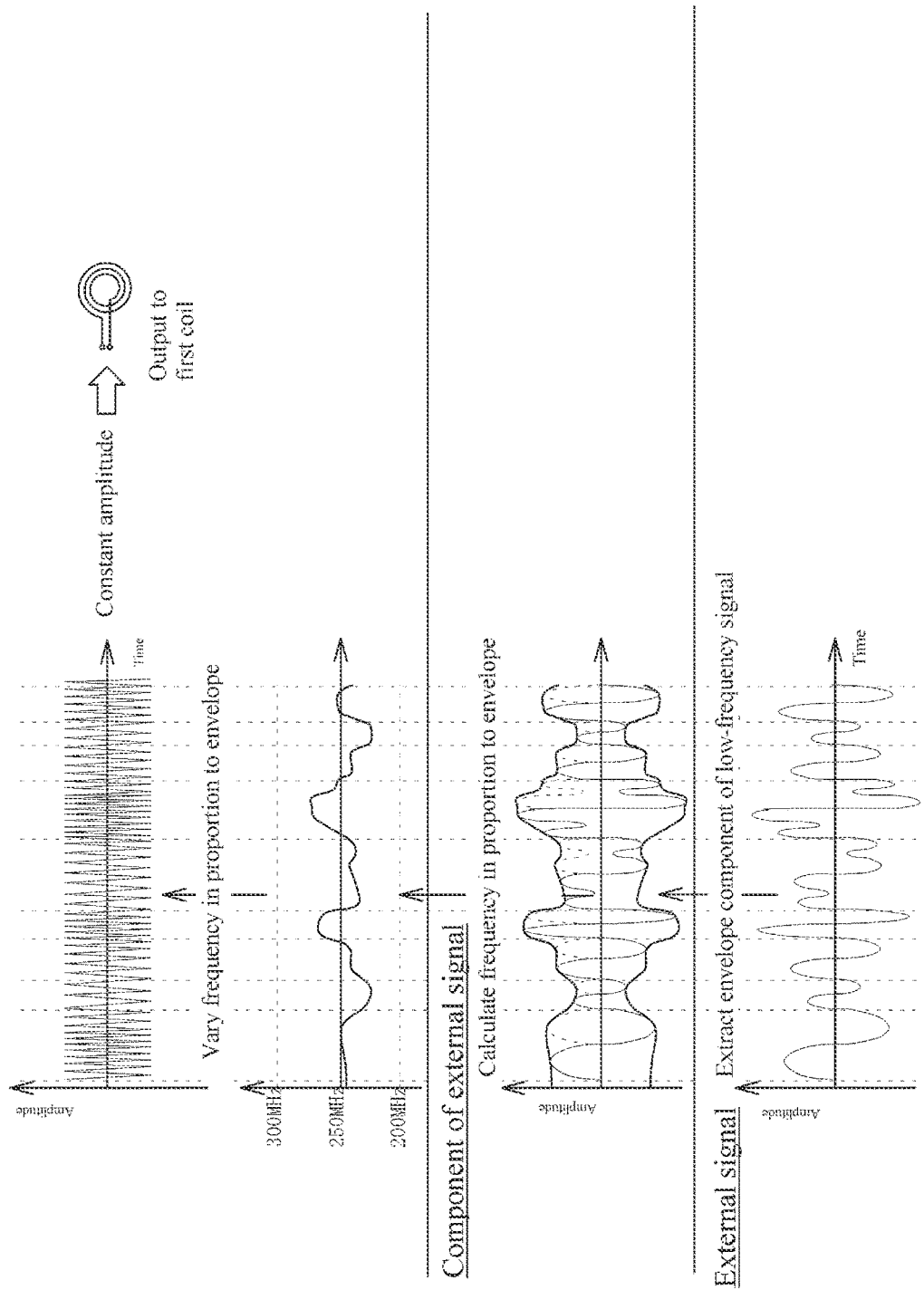
FIG. 7L is a view illustrating an example of generating the first biological stimulation signal wave having a frequency proportional to an envelope of the external signal by using the apparatus for generating signal waveform for biological stimulation of FIG. 1.
Figure 7M:
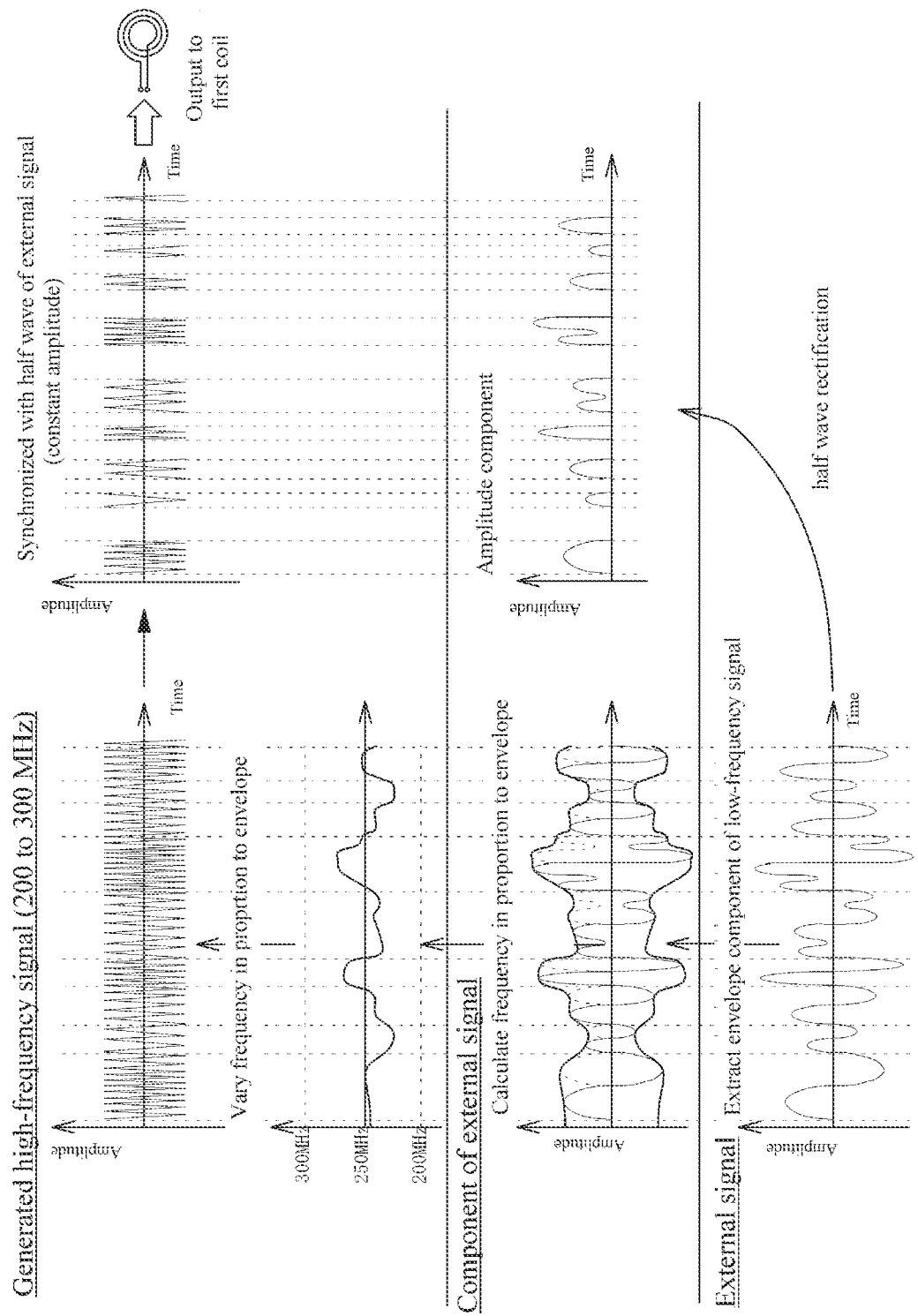
FIG. 7M is a view illustrating an example of generating the first biological stimulation signal wave having a frequency proportional to an envelope of the external signal synchronized with an output timing of a half wave of the external signal by using the apparatus for generating signal waveform for biological stimulation of FIG. 1.
Figure 7N:
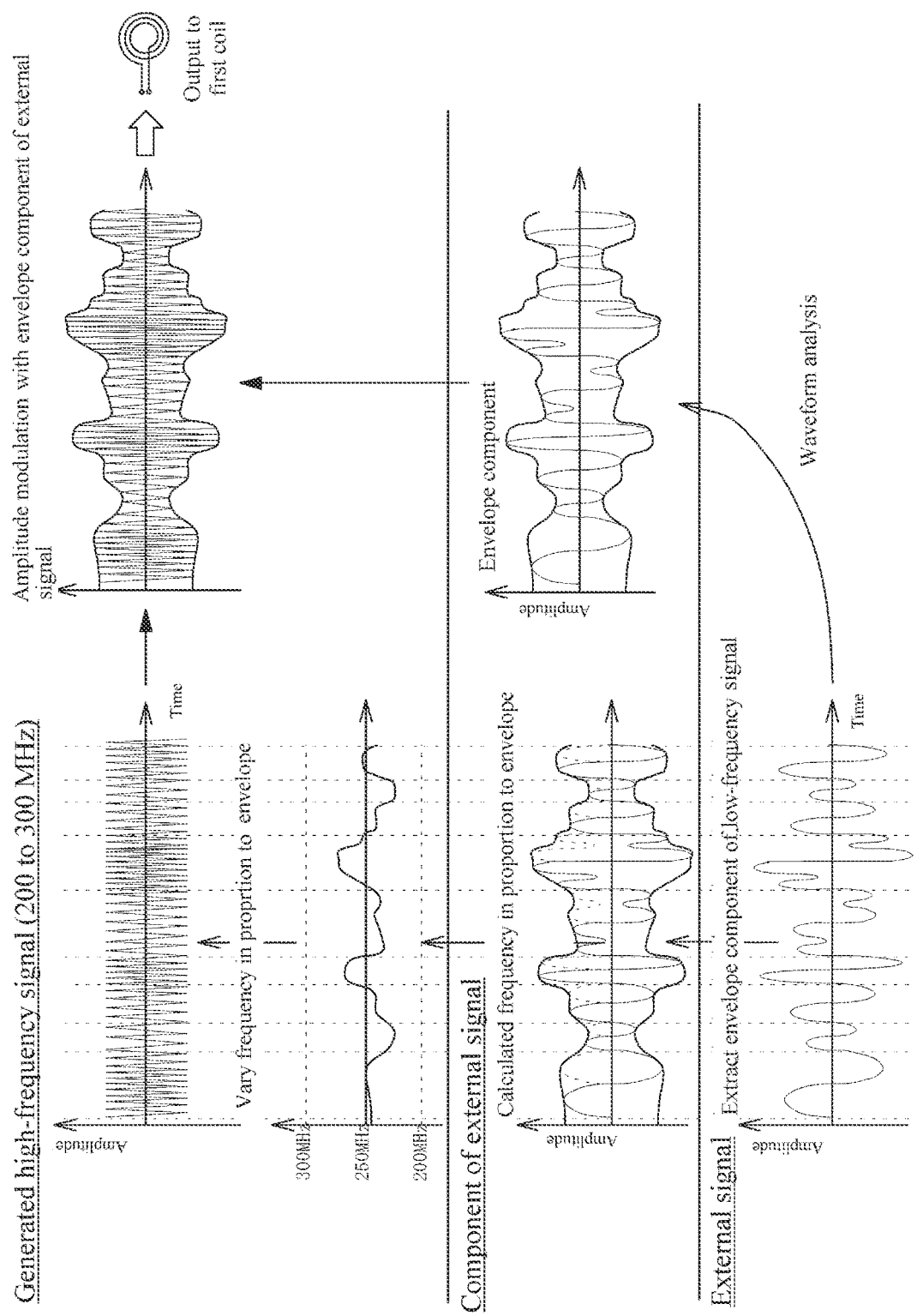
FIG. 7N is a view illustrating an example of generating the first biological stimulation signal wave having a frequency proportional to an envelope of the external signal subjected to amplitude modulation with the envelope by using the apparatus for generating signal waveform for biological stimulation of FIG. 1.
Figure 70:
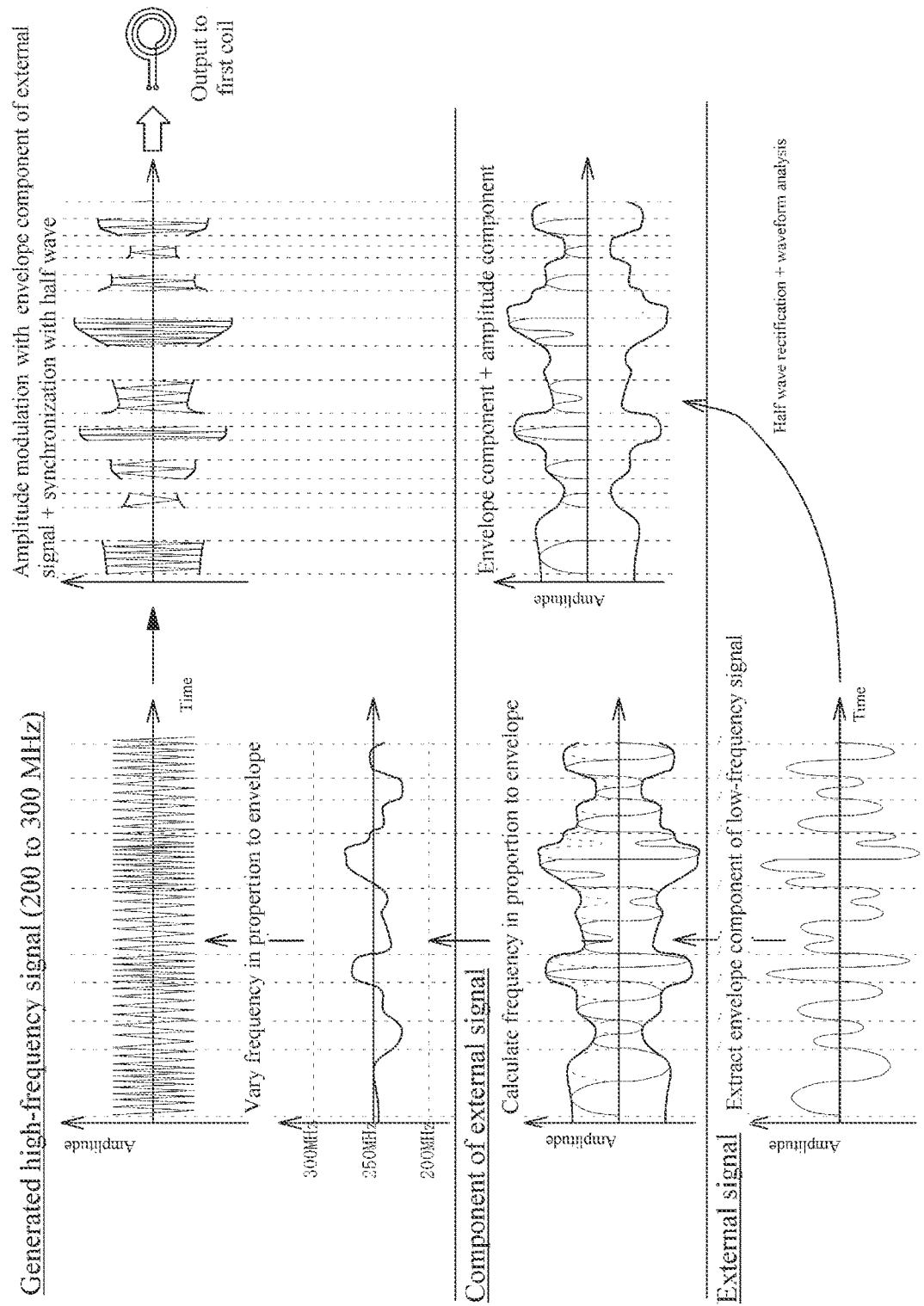
Figure 7P:
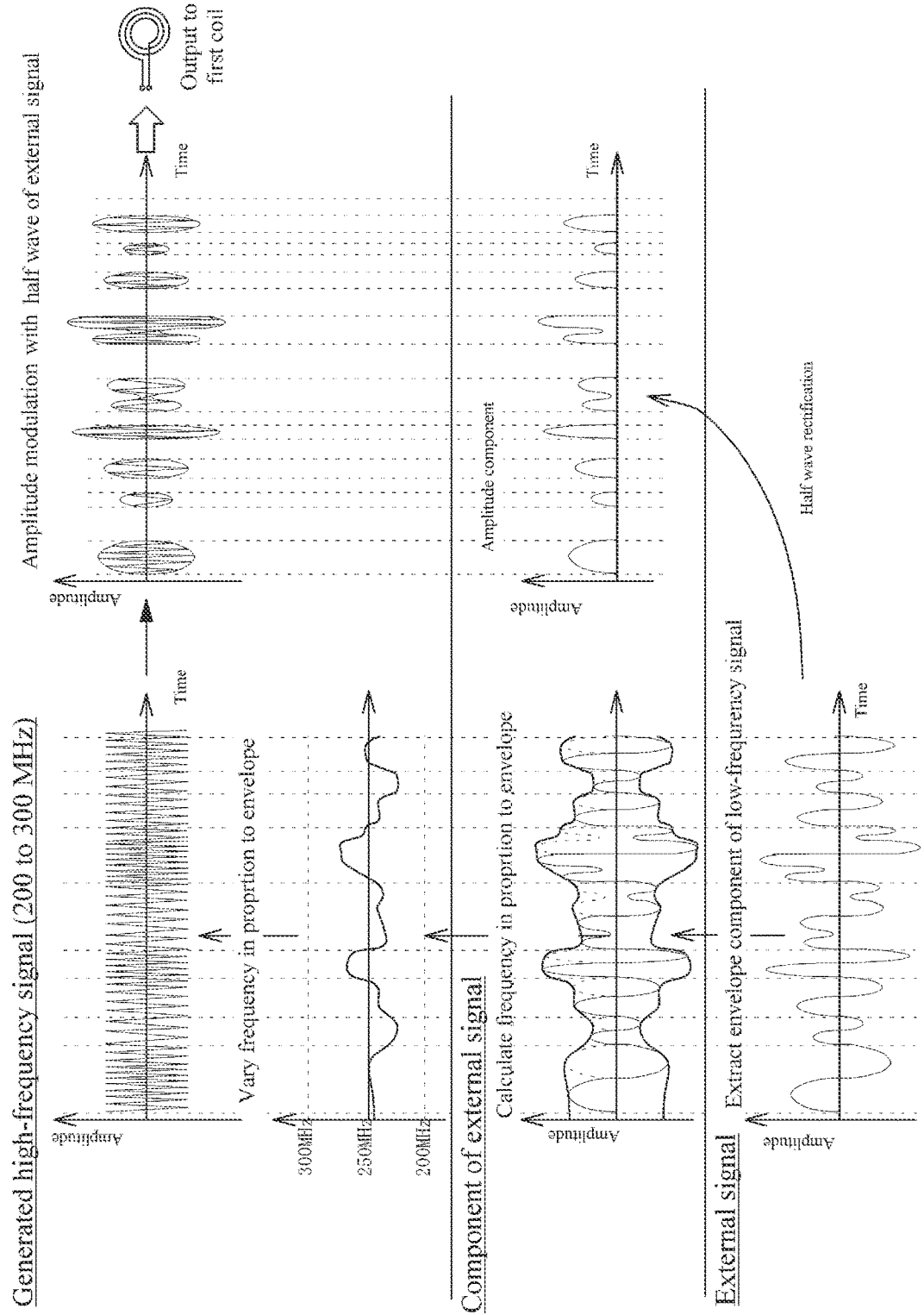
FIG. 7P is a view illustrating an example of generating the first biological stimulation signal wave having a frequency proportional to an envelope of the external signal subjected to amplitude modulation with a half wave of the external signal by using the apparatus for generating signal waveform for biological stimulation of FIG. 1.
Figure 7Q:
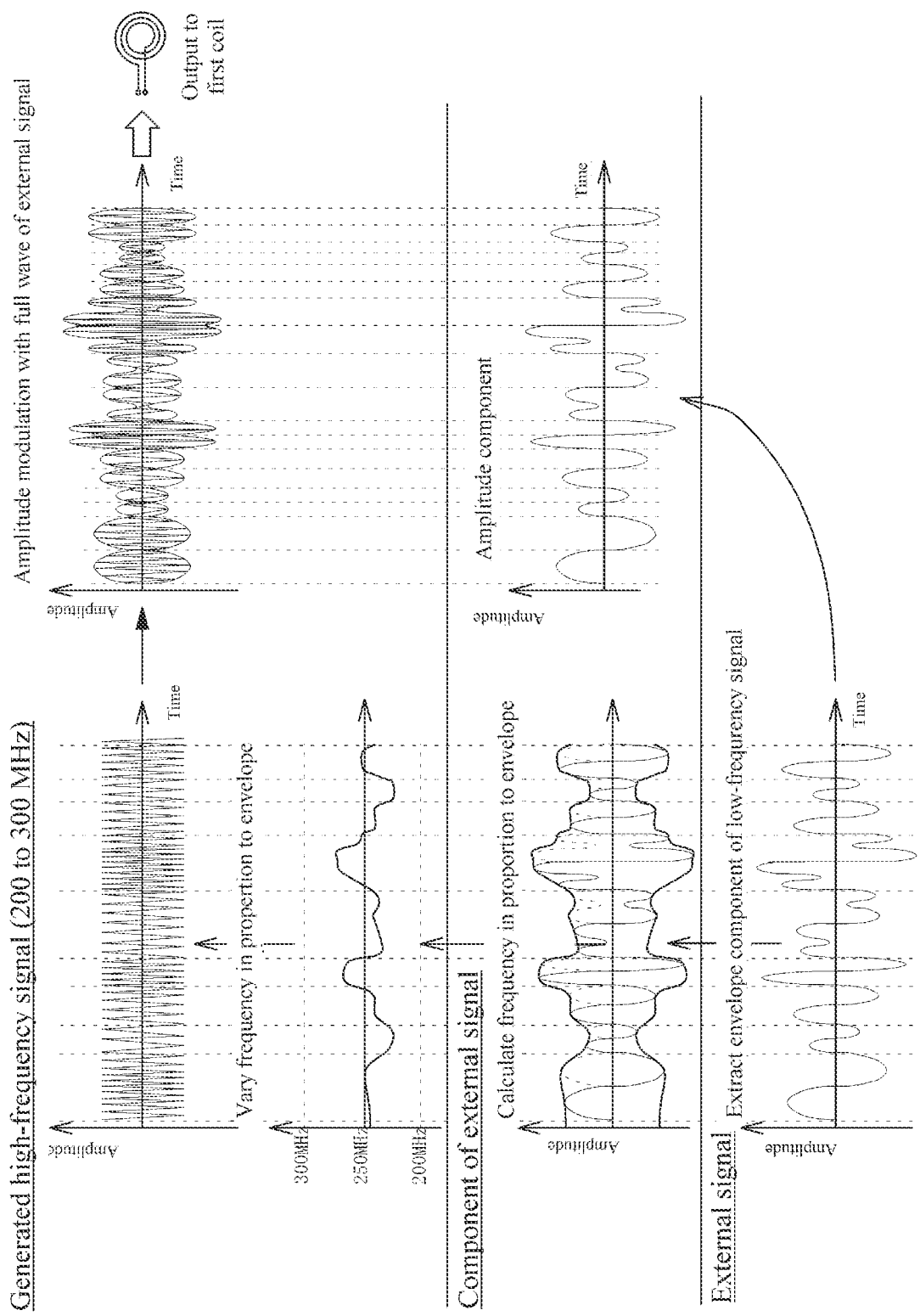
FIG. 7Q is a view illustrating an example of generating the first biological stimulation signal wave having a frequency proportional to an envelope of the external signal subjected to amplitude modulation with a full wave of the external signal by using the apparatus for generating signal waveform for biological stimulation of FIG. 1.
Figure 7R:
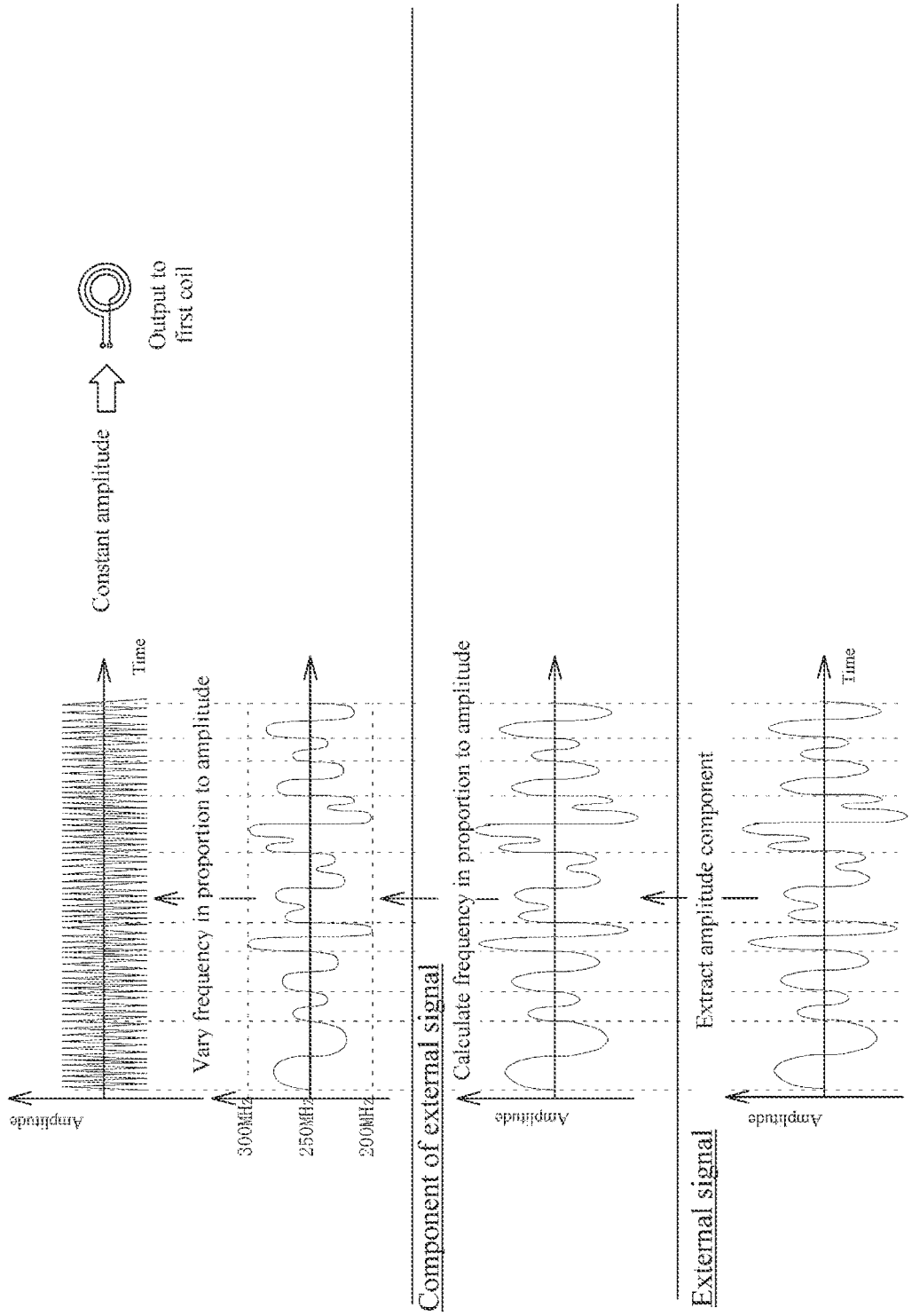
FIG. 7R is a view illustrating an example of generating the first biological stimulation signal wave with a frequency proportional to an amplitude of the external signal by using the apparatus for generating signal waveform for biological stimulation of FIG. 1.
Figure 7S:
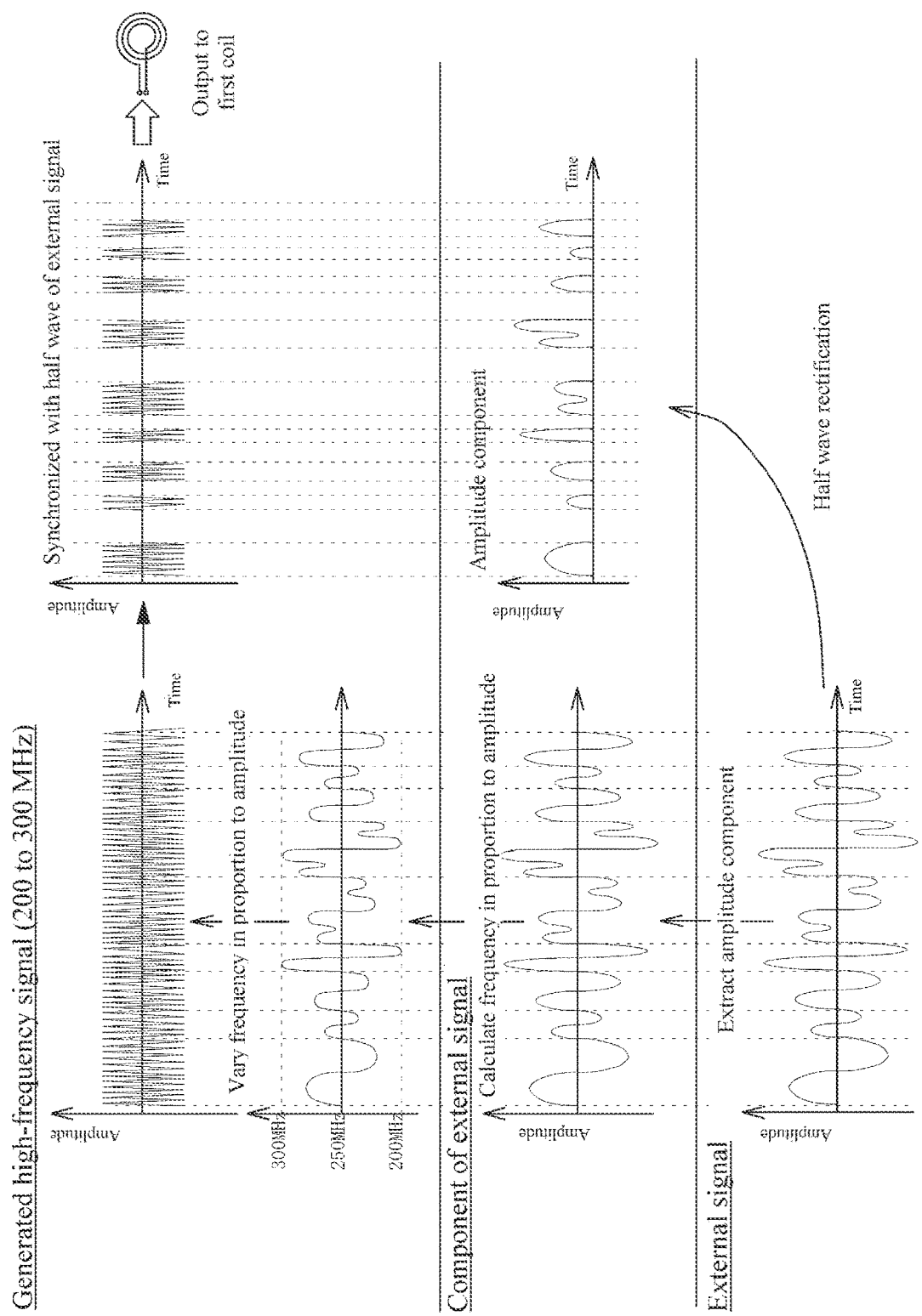
FIG. 7S is a view illustrating an example of generating the first biological stimulation signal wave having a frequency proportional to an amplitude of the external signal synchronized with an output timing of a half wave of the external signal by using the apparatus for generating signal waveform for biological stimulation of FIG. 1.
Figure 7T:
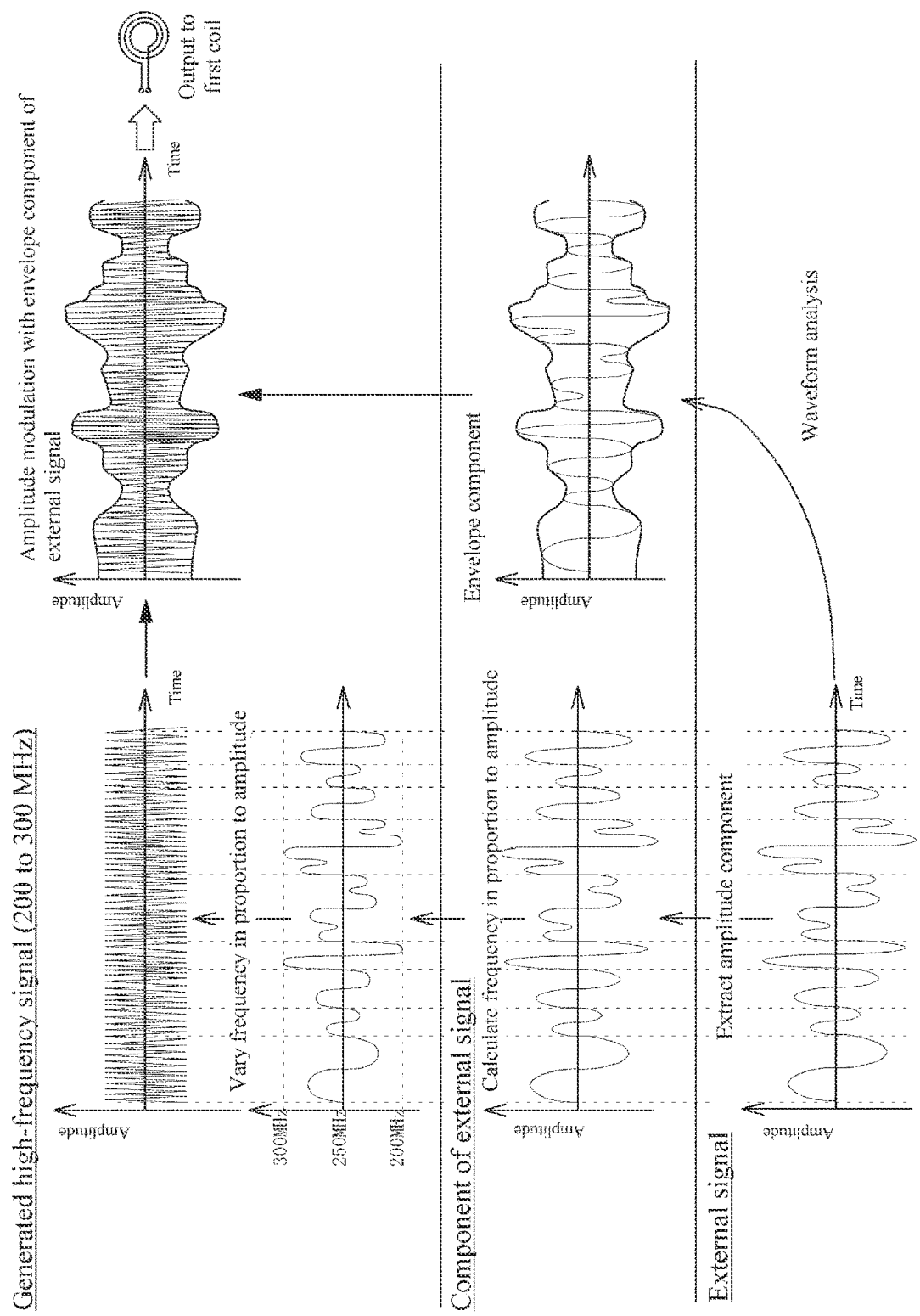
FIG. 7T is a view illustrating an example of generating the first biological stimulation signal wave having a frequency proportional to an amplitude of the external signal subjected to amplitude modulation with an envelope of the external signal by using the apparatus for generating signal waveform for biological stimulation of FIG. 1.
Figure 7U:
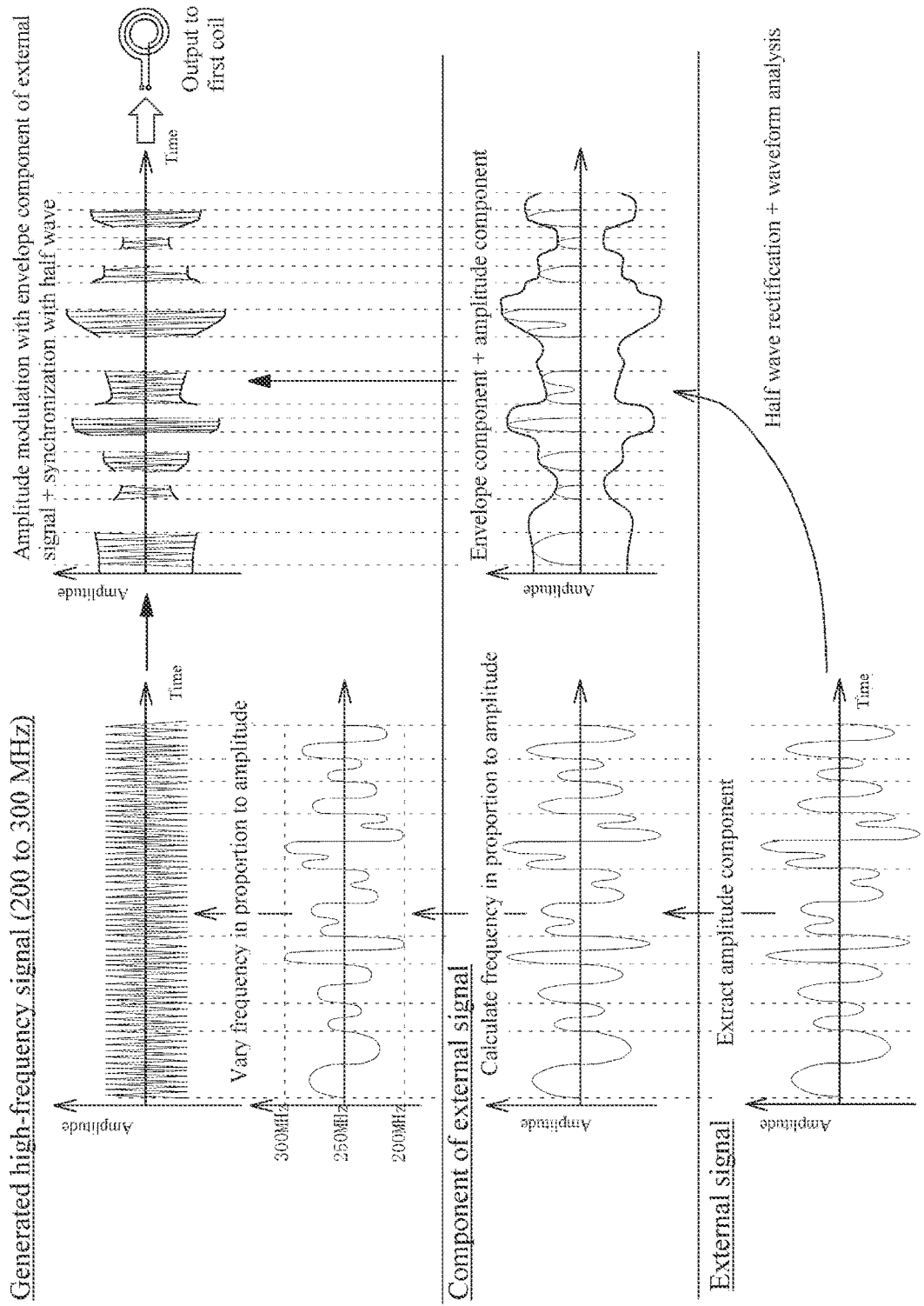
FIG. 7U is a view illustrating an example of generating the first biological stimulation signal wave having a frequency proportional to an amplitude of the external signal subjected to amplitude modulation with an envelope of the external signal by using the apparatus for generating signal waveform for biological stimulation of FIG. 1.
Figure 7V:
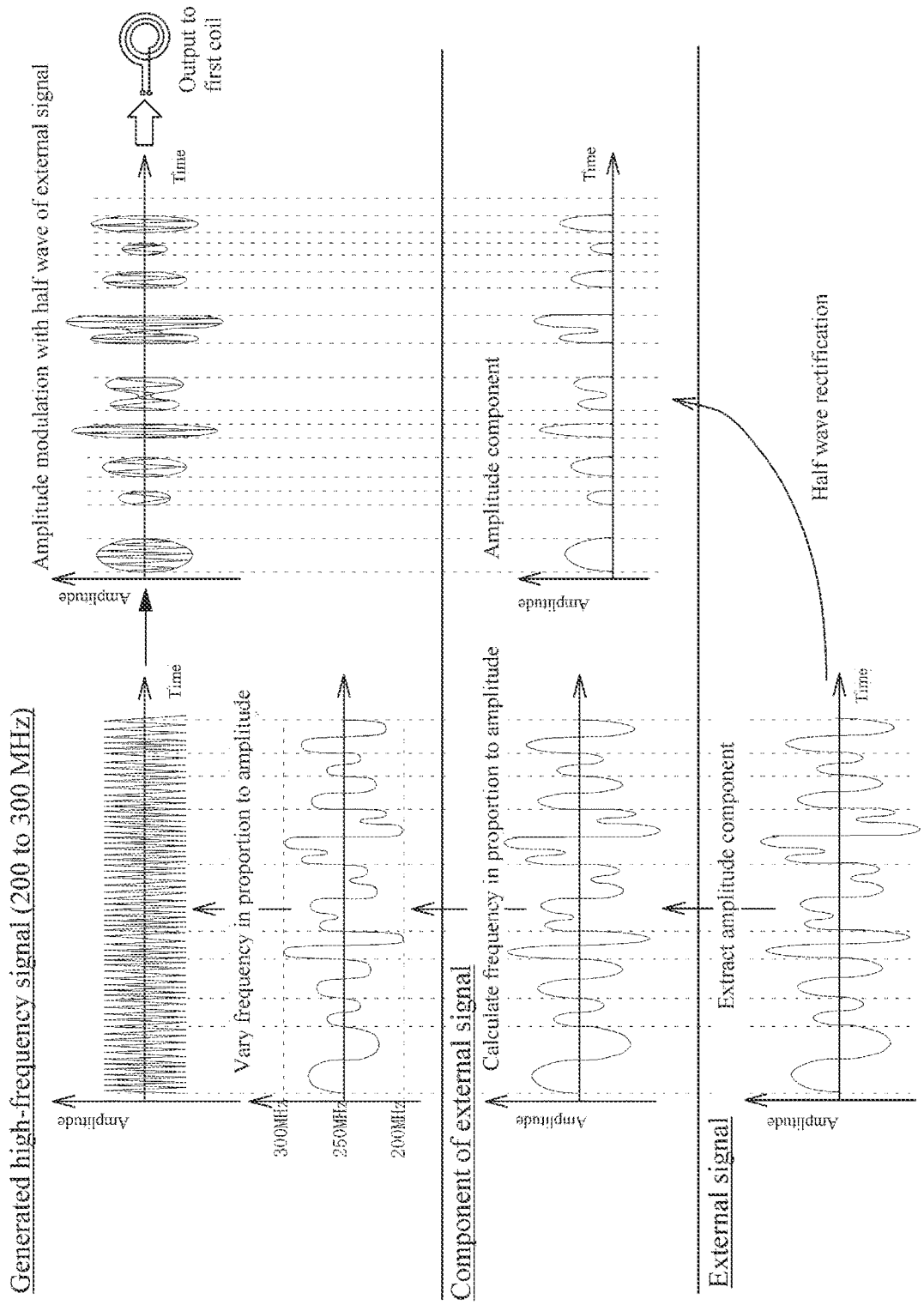
FIG. 7V is a view illustrating an example of generating the first biological stimulation signal wave having a frequency proportional to an amplitude of the external signal subjected to amplitude modulation with a half wave of the external signal by using the apparatus for generating signal waveform for biological stimulation of FIG. 1.
Figure 7W:
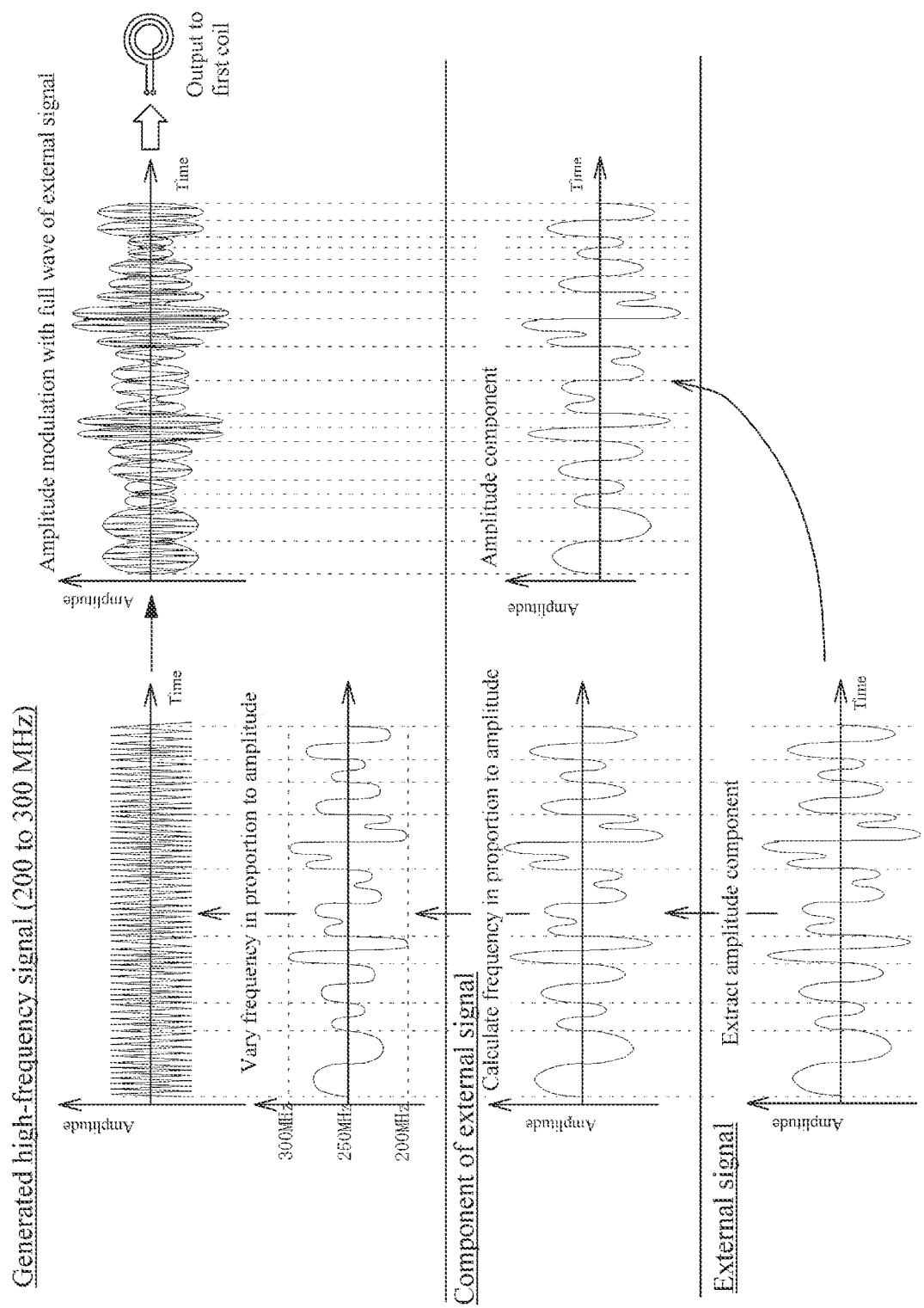
FIG. 7W is a view illustrating an example of generating the first biological stimulation signal wave having a frequency proportional to an amplitude of the external signal subjected to an amplitude modulation with a full wave of the external signal by using the apparatus for generating signal waveform for biological stimulation of FIG. 1.

FIGS. 7A to 7W show various waveform patterns of the first biological stimulation signal wave which can be generated through the signal wave generation unit 62 and the first output intensity adjustment unit 64 and reflects various components of the external signal.

In the example shown in FIG. 7A, a basic signal of a constant frequency (for example, 250 MHz) is generated in the signal wave generation unit 62, and an external signal of a low frequency such as 1 kHz to 3 kHz (for example, acoustic signal) is input from the signal source to the signal input unit 36. The input external signal is rectified to half wave in the waveform shaping unit 54. The basic signal with constant frequency and amplitude generated in the signal wave generation unit 62 is synchronized with an output timing of the external signal rectified to half wave in the first output intensity adjustment unit 64 and then output to the first coil 24 as the first biological stimulation signal wave.

In the example shown in FIG. 7B, a basic signal of a constant frequency (for example, 250 MHz) is generated in the signal wave generation unit 62 according to the example of FIG. 7A. An external signal of a low frequency such as 1 kHz to 3 kHz (for example, acoustic signal) is input from the signal source to the signal input unit 36. The input external signal is subjected to waveform analysis in the waveform analysis unit 56 to extract an envelope. The basic signal with the constant frequency and amplitude generated in the signal wave generation unit 62 is subjected to amplitude modulation with the envelope of the external signal in the first output intensity adjustment unit 64 and then output to the first coil 24 as the first biological stimulation signal wave.

In the example shown in FIG. 7C, a basic signal with a constant frequency (for example, 250 MHz) is generated in the signal wave generation unit 62 according to the example of FIG. 7A. An external signal of a low frequency such as 1 kHz to 3 kHz (for example, acoustic signal) is input from the signal source to the signal input unit 36. The input external signal is subjected to waveform analysis in the waveform analysis unit 56 to extract an envelope. The basic signal of the constant frequency and amplitude generated in the signal wave generation unit 62 is subjected to amplitude modulation with the envelope of the external signal in the first output intensity adjustment unit 64, synchronized with an output timing of the external signal rectified to half wave, and then output to the first coil 24 as the first biological stimulation signal wave.

In the example shown in FIG. 7D, a basic signal of a constant frequency (for example, 250 MHz) is generated in the signal wave generation unit 62 according to the example of FIG. 7A. An external signal of a low frequency such as 1 kHz to 3 kHz (for example, acoustic signal) is input from the signal source to the signal input unit 36. The input external signal is rectified to half wave in the waveform shaping unit 54. The basic signal of the constant frequency and amplitude generated in the signal wave generation unit 62 is subjected to amplitude modulation with the amplitude of the external signal rectified to half wave in the first output intensity adjustment unit 64 and then output to the first coil 24 as the first biological stimulation signal wave.

In the example shown in FIG. 7E, a basic signal of a constant frequency (for example, 250 MHz) is generated in the signal wave generation unit 62 according to the example of FIG. 7A. An external signal of a low frequency such as 1 kHz to 3 kHz (for example, acoustic signal) is input from the signal source to the signal input unit 36. The basic signal of the constant frequency and amplitude generated in the signal wave generation unit 62 is subjected to amplitude modulation with the amplitude (full wave) of the external signal in the first output intensity adjustment unit 64 and then output to the first coil 24 as the first biological stimulation signal wave.

In the example shown in FIG. 7F, an external signal of a low frequency such as 1 kHz to 3 kHz (for example, acoustic signal) is input from the signal source to the signal input unit 36. The frequency of the external signal is extracted in the waveform analysis unit 56. The extracted frequency of the external signal is converted to MHz band in the output waveform control unit 58, and the first biological stimulation signal wave of a high frequency proportional to the frequency of the external signal (for example, 30 MHz to 300 MHz, here 200 MHz to 300 MHz) is generated in the signal wave generation unit 62. The generated first biological stimulation signal wave of the high frequency is output at the constant amplitude to the first coil 24.

In the example shown in FIG. 7G, a high-frequency signal having a frequency proportional to the frequency of the external signal (for example, 30 MHz to 300 MHz, here 200 Hz to 300 MHz) is generated in the signal wave generation unit 62 according to the example of FIG. 7F. An external signal of a low frequency such as 1 kHz to 3 kHz (for example, acoustic signal) is input from the signal source to the signal input unit 36. The input external signal is rectified to half wave in the waveform shaping unit 54. The first biological stimulation signal wave generated in the signal wave generation unit 62 is synchronized with an output timing of the external signal rectified to half wave in the first output intensity adjustment unit 64 and then output to the first coil 24.

In the example shown in FIG. 7H, a high-frequency signal having a frequency proportional to the frequency of the external signal (for example, 30 MHz to 300 MHz, here 200 Hz to 300 MHz) is generated in the signal wave generation unit 62 according to the example of FIG. 7F. An external signal of a low frequency such as 1 kHz to 3 kHz (for example, acoustic signal) is input from the signal source to the signal input unit 36. The input external signal is subjected to waveform analysis in the waveform analysis unit 56 to extract an envelope. The first biological stimulation signal wave generated in the signal wave generation unit 62 is subjected to amplitude modulation with the envelope of the external signal in the first output intensity adjustment unit 64 and then output to the first coil 24.

In the example shown in FIG. 7I, the first biological stimulation signal wave having a high-frequency proportional to the frequency of the external signal (for example, 30 MHz to 300 MHz, here 200 Hz to 300 MHz) is generated in the signal wave generation unit 62 according to the example of FIG. 7F. An external signal of a low frequency such as 1 kHz to 3 kHz (for example, acoustic signal) is input from the signal source to the signal input unit 36. The input external signal is rectified to half wave in the waveform shaping unit 54 and subjected to waveform analysis in the waveform analysis unit 56 to extract an envelope. The first biological stimulation signal wave generated in the signal wave generation unit 62 is subjected to amplitude modulation with the envelope of the external signal as well as synchronization processing with an output timing of the external signal rectified to half wave in the first output intensity adjustment unit 64, and then output to the first coil 24.

In the example shown in FIG. 7J, the first biological stimulation signal wave having a high-frequency proportional to the frequency of the external signal (for example, 30 MHz to 300 MHz, here 200 Hz to 300 MHz) is generated in the signal wave generation unit 62 according to the example of FIG. 7F. An external signal of a low frequency such as 1 kHz to 3 kHz (for example, acoustic signal) is input from the signal source to the signal input unit 36. The input external signal is rectified to half wave in the waveform shaping unit 54. The first biological stimulation signal wave generated in the signal wave generation unit 62 is subjected to amplitude modulation with the external signal rectified to half wave in the first output intensity adjustment unit 64 and then output to the first coil 24.

In the example shown in FIG. 7K, the first biological stimulation signal wave having a high-frequency proportional to the frequency of the external signal (for example, 30 MHz to 300 MHz, here 200 Hz to 300 MHz) is generated in the signal wave generation unit 62 according to the example of FIG. 7F. An external signal of a low frequency such as 1 kHz to 3 kHz (for example, acoustic signal) is input from the signal source to the signal input unit 36. The first biological stimulation signal wave generated in the signal wave generation unit 62 is subjected to amplitude modulation with the external signal (full wave) in the first output intensity adjustment unit 64 and then output to the first coil 24.

In the example shown in FIG. 7L, an external signal of, for example, 1 kHz to 3 kHz (for example, acoustic signal) is input from the signal source to the signal input unit 36. An envelope of the external signal is extracted in the waveform analysis unit 56. A frequency of MHz band proportional to the extracted envelope of the external signal is calculated in the output waveform control unit 58, and the first biological stimulation signal wave with a high frequency proportional to the extracted envelope of the external signal (for example, 30 MHz to 300 MHz, here 200 MHz to 300 MHz) is generated in the signal wave generation unit 62. The generated first biological stimulation signal wave is output at a constant amplitude to the first coil 24.

In the example shown in FIG. 7M, the first biological stimulation signal wave of a high frequency proportional to the envelope of the external signal (for example, 30 MHz to 300 MHz, here 200 MHz to 300 MHz) is generated in the signal wave generation unit 62 according to the example of FIG. 7L. The external signal input to the signal input unit 36 is rectified to half wave in the waveform shaping unit 54. The first biological stimulation signal wave generated in the signal wave generation unit 62 is synchronized with an output timing of the external signal rectified to half wave in the first output intensity adjustment unit 64 and then output to the first coil 24.

In the example shown in FIG. 7N, the first biological stimulation signal wave of a high frequency proportional to the envelope of the external signal (for example, 30 MHz to 300 MHz, here 200 MHz to 300 MHz) is generated in the signal wave generation unit 62 according to the example of FIG. 7L. The first biological stimulation signal wave generated in the signal wave generation unit 62 is subjected to amplitude modulation with the envelope of the external signal in the first output intensity adjustment unit 64 and then output to the first coil 24.

In the example shown in FIG. 7O, the first biological stimulation signal wave of a high frequency proportional to the envelope of the external signal (for example, 30 MHz to 300 MHz, here 200 MHz to 300 MHz) is generated in the signal wave generation unit 62 according to the example of FIG. 7L. The external signal input to the signal input unit 36 is rectified to half wave in the waveform shaping unit 54. The first biological stimulation signal wave generated in the signal wave generation unit 62 is subjected to amplitude modulation with the envelope of the external signal as well as synchronization processing with an output timing of the external signal rectified to half wave in the first output intensity adjustment unit 64 and then output to the first coil 24.

In the example shown in FIG. 7P, the first biological stimulation signal wave of a high frequency proportional to the envelope of the external signal (for example, 30 MHz to 300 MHz, here 200 MHz to 300 MHz) is generated in the signal wave generation unit 62 according to the example of FIG. 7L. The external signal input to the signal input unit 36 is rectified to half wave in the waveform shaping unit 54. The first biological stimulation signal wave generated in the signal wave generation unit 62 is subjected to amplitude modulation with the external signal rectified to half wave in the first output intensity adjustment unit 64 and then output to the first coil 24.

In the example shown in FIG. 7Q, the first biological stimulation signal wave of a high frequency proportional to the envelope of the external signal (for example, 30 MHz to 300 MHz, here 200 MHz to 300 MHz) is generated in the signal wave generation unit 62 according to the example of FIG. 7L. The first biological stimulation signal wave generated in the signal wave generation unit 62 is subjected to amplitude modulation with the external signal (full wave) in the first output intensity adjustment unit 64 and then output to the first coil 24.

In the example shown in FIG. 7R, an external signal of a low frequency such as 1 kHz to 3 kHz (for example, acoustic signal) is input from the signal source to the signal input unit 36. An amplitude of the external signal is extracted in the waveform analysis unit 56. A frequency of MHz band proportional to the extracted amplitude of the external signal is calculated in the output waveform control unit 58, and the first biological stimulation signal wave of a high frequency proportional to the amplitude of the external signal (for example, 30 MHz to 300 MHz, here 200 MHz to 300 MHz) is generated in the signal wave generation unit 62. The generated first biological stimulation signal wave is output at a constant amplitude to the first coil 24.

In the example shown in FIG. 7S, the first biological stimulation signal wave of a high frequency proportional to the amplitude of the low-frequency external signal (for example, 30 MHz to 300 MHz, here 200 MHz to 300 MHz) is generated in the signal wave generation unit 62 according to the example of FIG. 7R. The external signal input to the signal input unit 36 is rectified to half wave in the waveform shaping unit 54. The first biological stimulation signal wave generated in the signal wave generation unit 62 is synchronized with an output timing of the external signal rectified to half wave in the first output intensity adjustment unit 64 and then output to the first coil 24.

In the example shown in FIG. 7T, the first biological stimulation signal wave of a high frequency proportional to the amplitude of the low-frequency external signal (for example, 30 MHz to 300 MHz, here 200 MHz to 300 MHz) is generated in the signal wave generation unit 62 according to the example of FIG. 7R. The external signal input to the signal input unit 36 is subjected to waveform analysis in the waveform analysis unit 56 to extract an envelope. The first biological stimulation signal wave generated in the signal wave generation unit 62 is subjected to amplitude modulation with the envelope of the external signal in the first output intensity adjustment unit 64 and output to the first coil 24.

In the example shown in FIG. 7U, the first biological stimulation signal wave of a high frequency proportional to the amplitude of the low-frequency external signal (for example, 30 MHz to 300 MHz, here 200 MHz to 300 MHz) is generated in the signal wave generation unit 62 according to the example of FIG. 7R. The external signal input to the signal input unit 36 is rectified to half wave in the waveform shaping unit 54. The first biological stimulation signal wave generated in the signal wave generation unit 62 is subjected to amplitude modulation with the envelope of the external signal as well as synchronization processing with an output timing of the external signal rectified to half wave in the first output intensity adjustment unit 64, and then output to the first coil 24.

In the example shown in FIG. 7V, the first biological stimulation signal wave of a high frequency proportional to the amplitude of the low-frequency external signal (for example, 30 MHz to 300 MHz, here 200 MHz to 300 MHz) is generated in the signal wave generation unit 62 according to the example of FIG. 7R. The external signal input to the signal input unit 36 is rectified to half wave in the waveform shaping unit 54. The first biological stimulation signal wave generated in the signal wave generation unit 62 is subjected to amplitude modulation with the external signal rectified to half wave in the first output intensity adjustment unit 64 and the output to the first coil 24.

In the example shown in FIG. 7W, the first biological stimulation signal wave of a high frequency proportional to the amplitude of the low-frequency external signal (for example, 30 MHz to 300 MHz, here 200 MHz to 300 MHz) is generated in the signal wave generation unit 62 according to the example of FIG. 7R. The first biological stimulation signal wave generated in the signal wave generation unit 62 is subjected to amplitude modulation with the external signal (full wave) in the first output intensity adjustment unit 64 and then output to the first coil 24.

As mentioned above, the apparatus for generating signal waveform for biological stimulation according to the above embodiments is constructed in such a manner that the first biological stimulation signal wave modulated with at least one of frequency component, envelope component and amplitude component of the external signal, which may be of a low frequency, and/or synchronized with the output timing of the external signal is generated in the output waveform generation unit 12, so that waveform features and/or synchronization performance related to the external signal can be applied to an alternating magnetic field generated from the first coil and based on the first biological stimulation signal wave. Also, the second biological stimulation signal wave is fed to the second coil 26 based on the external signal to generate an alternating magnetic field based on the second biological stimulation signal wave. Here, the alternating magnetic field of a low frequency such as 1 kHz to 3 kHz band is transferred to sensory nerve (A β fiber: haptic sense) and arrives at spinal dorsal horn and brain (sensory area), whereby it is expected that when good feeling of haptic sense is recognized by the brain, a descending pain inhibitory system is activated to produce analgesic effect or relaxation effect. On the other hand, the alternating magnetic field of a high frequency such as 30 MHz to 300 MHz, preferably 200 MHz to 300 MHz, more preferably 250 MHz band activates a damaged sensory cell and induces a neurotrophic factor, which is expected to have an effect of mitigating nerve damage. Further, features relating to the waveform of the low-frequency alternating magnetic field is applied to the waveform of the high-frequency alternating magnetic field to cause synergistic action, whereby a higher analgesic effect or the like is expected.

Also, the second coil 26 and the first coil 24 are arranged so as to overlap with each other viewing from the axial line of the coil, whereby the above synergistic action is developed more effectively to expect a higher analgesic effect or the like.

Furthermore, a further higher analgesic effect or the like is expected by irradiating the low-frequency magnetic field and the high-frequency magnetic field to a wide range inclusive of an affected area with plural sets of second coils 26 and first coils 24.

In the apparatus for generating signal waveform for biological stimulation according to this embodiment, the haptic output unit 22 for outputting the low-frequency external signal as sound, image and/or oscillation is arranged, whereby it is expected to give a relaxation effect to a patient based on body sensory stimulation and mitigate brain tension or stress state by pain to enhance a relief effect synergistically. For example, by applying magnetic stimulation to an affected area with the first coil 24 and the second coil 26 by using Mozart's motet, "Exsultate Jubilate", as a sound source for the low-frequency external signal and outputting the sound from a speaker 28 to have a patient hear, it is expected to increase a wave and also improve an analgesic effect or the like by a subjective feeling of pain score (VAS) and a pain threshold test.

Further, the high-frequency alternating magnetic field and the low-frequency alternating magnetic field can be changed at a fluctuation cycle of 1/f pitch by using a signal having a fluctuation feature of 1/f tone as a low-frequency external signal, whereby it is expected to increase a-wave and, along with it, improve the analgesic effect or the like by the VAS and pain threshold test.

Although the present invention is described based on the above embodiments and examples, the invention is not limited to these embodiments and it is possible to conduct various additions, modifications and corrections within a range of claims. For example, an example of applying magnetic stimulation to a biological body with the first biological stimulation signal wave and the second biological stimulation signal wave generated by the apparatus for generating signal waveform for biological stimulation is shown in the above embodiments, but electric signal, light stimulation, sound stimulation, oscillation stimulation or temperature stimulation may be used. In the light stimulation, although there are differences between individuals as a result of a flicker test, stimulation is felt up to about 30 Hz, but is not substantially felt at 50 Hz, so that an illuminating device such as LED or the like can be blinked and a brightness can be changed in synchrony with an intensity of the signal in addition that the first generated biological stimulation signal wave is compressed to 0 Hz to 30 Hz (0 is not included). Also, since the sound or oscillation stimulation is a form called as body sonic, 50 Hz to 150 Hz is a band connecting to sound and supplementing reality of sound and 20 Hz to 50 Hz is a band producing a feeling of presence, a feeling of euphoria and a physiological comfortable feeling, so that they can be used in the sound or oscillation stimulation in addition that the first generated biological stimulation signal wave is compressed to 20 Hz to 150 Hz.

INDUSTRIAL APPLICABILITY

According to the invention, there can be provided the apparatus for generating signal waveform for biological stimulation which can generate and output biological stimulation signal waves from signals existing in the external environment such as sunbeams streaming through leaves, murmuring of river, comfortable music or favorite music. Mother's heart sound and the like and reflecting these signals.

REFERENCE SIGNS LIST 10 input unit
11 input signal processing unit
12 output waveform generation unit
13 output unit
14 operation unit
15 screen display device
16 action instruction unit
20 coil output unit
22 haptic output unit
24 first coil (coil for high frequency)
26 second coil (coil for low frequency)
30 image reproduction device
32 image display device
34 oscillation generation device
36 signal input unit
38 light sensor
40 acoustic sensor
42 acoustic reproduction device
44 biological signal detection device
46 storage unit
50 changeover switch
52 input signal amplitude adjustment unit
54 waveform shaping unit
56 waveform analysis unit
58 output waveform control unit
60 output adjustment unit
62 signal wave generation unit
64 first output intensity adjustment unit
66 second output intensity adjustment unit
68 oscillator for kHz band
70 oscillator for 7.8 Hz band
72 first synchronization switching unit
74 first output switching unit
76 waveform switching unit
78 second synchronization switching unit
80 second output switching unit

The invention claimed is:
1. An apparatus for generating signal waveform for biological stimulation, comprising:
a signal input unit for inputting an external signal from an external environment;
a controller configured to generate and output:
a first biological stimulation signal wave that is
(a) frequency modulated by at least one of:
(x) a frequency component included in the external signal,
(y) an envelope component included in the external signal, and
(z) an amplitude component included in the external signal; and/or
(b) synchronized with an output timing of the external signal; and
a second biological stimulation signal wave based on the external signal;
a memory configured to store:
the external signal; and/or
the frequency component, envelope component and amplitude component included in the external signal;
a first coil for generating a high-frequency alternate magnetic field by feeding of the first biological stimulation signal wave;
a second coil for generating a low-frequency alternate magnetic field by feeding of the second biological stimulation signal wave; and
a haptic output unit comprising at least one of a speaker configured to output the external signal as a sound and a display configured to output the external signal as an image, wherein the first coil and the second coil overlap with each other viewed along an axis of the first coil and an axis of the second coil, the high-frequency alternate magnetic field is in a range of 30 MHz to 300 MHz, the low-frequency alternate magnetic field is in a range of 1 kHz to 3 kHz, and features of the waveform of the low-frequency alternate magnetic field are applied to the waveform of the high-frequency alternate magnetic field.

2. The apparatus for generating signal waveform for biological stimulation according to claim 1, wherein the controller is configured to subject the first biological stimulation signal wave to amplitude modulation by at least one of the envelope component and the amplitude component included in the external signal.

3. The apparatus for generating signal waveform for biological stimulation according to claim 1, wherein the high-frequency alternate magnetic field is configured to cause stimulation by activating a damaged sensory cell and mitigating a nerve damage by inducing a neurotrophic factor, and the low-frequency magnetic field is configured to cause stimulation by sending the second biological stimulation signal wave from a sensory nerve, through a spinal dorsal horn and to a brain.

4. The apparatus for generating signal waveform for biological stimulation according to claim 1, wherein the haptic output unit further comprises an oscillation generation device configured to output the external signal as an oscillation.

5. The apparatus for generating signal waveform for biological stimulation according to claim 3, wherein the haptic output unit further comprises an oscillation generation device configured to output the external signal as an oscillation.

6. The apparatus for generating signal waveform for biological stimulation according to claim 1, wherein the external signal is a sound signal of an audible frequency band.

7. The apparatus for generating signal waveform for biological stimulation according to claim 3, wherein the external signal is a sound signal of an audible frequency band.

8. The apparatus for generating signal waveform for biological stimulation according to claim 1, wherein the features of the waveform of the low-frequency alternate magnetic field are at least one of frequency, envelope and amplitude.

9. An apparatus for generating signal waveform for biological stimulation, comprising:
- a signal input unit for inputting an external signal from an external environment, wherein the external signal is a sound signal of an audible frequency band;
- a controller configured to generate and output:
  - a first biological stimulation signal wave that is
  - (a) frequency modulated by at least one of:
    - (x) a frequency component included in the external signal,
    - (y) an envelope component included in the external signal, and
    - (z) an amplitude component included in the external signal; and/or
  - (b) synchronized with an output timing of the external signal; and
  - a second biological stimulation signal wave based on the external signal;
- a first coil for generating a high-frequency alternate magnetic field by feeding of the first biological stimulation signal wave;
- a second coil for generating a low-frequency alternate magnetic field by feeding of the second biological stimulation signal wave;
- a haptic output unit comprising at least one of a speaker configured to output the external signal as a sound and a display configured to output the external signal as an image, wherein the first coil and the second coil overlap with each other viewed along an axis of the first coil and an axis of the second coil, the high-frequency alternate magnetic field is in a range of 30 MHz to 300 MHz, the low-frequency alternate magnetic field is in a range of 1 kHz to 3 kHz, and features of the waveform of the low-frequency alternate magnetic field are applied to the waveform of the high-frequency alternate magnetic field.

* * * * *